(12) United States Patent
Zhang et al.

(10) Patent No.: US 9,149,639 B2
(45) Date of Patent: Oct. 6, 2015

(54) SYSTEMS FOR USING A PULMONARY ARTERY ELECTRODE

(71) Applicant: Cardiac Pacemakers, Inc., St. Paul, MN (US)

(72) Inventors: Yongxing Zhang, Irvine, CA (US); Yunlong Zhang, Mounds View, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/855,570

(22) Filed: Apr. 2, 2013

(65) Prior Publication Data
US 2013/0218221 A1    Aug. 22, 2013

Related U.S. Application Data

(63) Continuation of application No. 12/779,177, filed on May 13, 2010, now Pat. No. 8,417,354, which is a continuation of application No. 11/125,997, filed on May 10, 2005, now Pat. No. 7,734,348.

(51) Int. Cl.
*A61N 1/36* (2006.01)
*A61N 1/365* (2006.01)
*A61N 1/368* (2006.01)
(Continued)

(52) U.S. Cl.
CPC ............. *A61N 1/365* (2013.01); *A61N 1/368* (2013.01); *A61N 1/395* (2013.01); *A61N 1/3605* (2013.01); *A61N 1/3622* (2013.01); *A61N 1/3624* (2013.01);
(Continued)

(58) Field of Classification Search
CPC ................ A61N 1/05; A61N 1/0573; A61N 2007/0021; A61N 1/3605

USPC ........................................................ 607/9, 14
See application file for complete search history.

(56) References Cited

U.S. PATENT DOCUMENTS 3,650,277 A    3/1972  Sjostrand et al.
4,730,619 A    3/1988  Koning et al.
(Continued)

FOREIGN PATENT DOCUMENTS

CN    1819855 A    8/2006
JP    05269210     10/1993
(Continued)

OTHER PUBLICATIONS

U.S. Appl. No. 10/745,921, Advisory Action mailed Feb. 13, 2007, 5 pgs.
(Continued)

*Primary Examiner* — Christopher D Koharski
*Assistant Examiner* — Natasha Patel
(74) *Attorney, Agent, or Firm* — Faegre Baker Daniels LLP

(57) ABSTRACT

According to some method embodiments, a left pulmonary artery electrode is positioned in a left pulmonary artery, and the left pulmonary artery electrode is used to sense atrial activity, or capture cardiac tissue, or deliver neural stimulation. According to some method embodiments, a right pulmonary artery electrode is positioned in a right pulmonary artery and a left pulmonary artery electrode is positioned in a left pulmonary artery, the right pulmonary artery electrode is used to sense atrial activity, or capture cardiac tissue, or deliver neural stimulation, and the left pulmonary artery electrode is used to sense atrial activity, or capture cardiac tissue, or deliver neural stimulation.

11 Claims, 11 Drawing Sheets

(51) Int. Cl.
*A61N 1/39* (2006.01)
*A61N 1/362* (2006.01)

(52) U.S. Cl.
CPC .......... *A61N 1/3627* (2013.01); *A61N 1/36114* (2013.01); *A61N 1/3956* (2013.01)

(56) References Cited

U.S. PATENT DOCUMENTS

| | | | |
|---|---|---|---|
| 5,144,960 | A | 9/1992 | Mehra et al. |
| 5,199,428 | A | 4/1993 | Obel et al. |
| 5,203,326 | A | 4/1993 | Collins |
| 5,243,980 | A | 9/1993 | Mehra |
| 5,334,221 | A | 8/1994 | Bardy |
| 5,403,351 | A | 4/1995 | Saksena |
| 5,409,009 | A | 4/1995 | Olson |
| 5,690,681 | A | 11/1997 | Geddes et al. |
| 5,707,400 | A | 1/1998 | Terry, Jr. et al. |
| 5,769,881 | A | 6/1998 | Schroeppel et al. |
| 6,006,122 | A | 12/1999 | Smits |
| 6,073,048 | A | 6/2000 | Kieval et al. |
| 6,076,014 | A | 6/2000 | Alt |
| 6,141,588 | A | 10/2000 | Cox et al. |
| 6,178,349 | B1 | 1/2001 | Kieval |
| 6,208,894 | B1 | 3/2001 | Schulman et al. |
| 6,292,695 | B1 | 9/2001 | Webster, Jr. et al. |
| 6,470,211 | B1 | 10/2002 | Ideker et al. |
| 6,522,926 | B1 | 2/2003 | Kieval et al. |
| 6,574,512 | B1 | 6/2003 | Zhang et al. |
| 6,584,362 | B1 | 6/2003 | Scheiner et al. |
| 6,882,886 | B1 | 4/2005 | Witte et al. |
| 7,058,450 | B2 | 6/2006 | Struble et al. |
| 7,236,821 | B2 | 6/2007 | Cates et al. |
| 7,292,888 | B2 | 11/2007 | Deno et al. |
| 7,493,161 | B2 | 2/2009 | Libbus et al. |
| 7,521,322 | B2 | 4/2009 | Tang et al. |
| 7,643,875 | B2 | 1/2010 | Hiel, Jr. et al. |
| 7,734,348 | B2 | 6/2010 | Zhang et al. |
| 7,765,000 | B2 | 7/2010 | Zhang et al. |
| 8,417,354 | B2 | 4/2013 | Zhang et al. |
| 8,527,064 | B2 | 9/2013 | Zhang et al. |
| 2002/0026222 | A1 | 2/2002 | Schauerte et al. |
| 2002/0026228 | A1 | 2/2002 | Schauerte |
| 2002/0120304 | A1* | 8/2002 | Mest ............... 607/14 |
| 2002/0188326 | A1 | 12/2002 | Zheng et al. |
| 2003/0060858 | A1 | 3/2003 | Kieval et al. |
| 2003/0078623 | A1* | 4/2003 | Weinberg et al. ........ 607/9 |
| 2003/0125770 | A1 | 7/2003 | Fuimaono et al. |
| 2003/0158584 | A1 | 8/2003 | Cates et al. |
| 2004/0199210 | A1 | 10/2004 | Shelchuk |
| 2004/0215289 | A1 | 10/2004 | Fukui |
| 2005/0010263 | A1 | 1/2005 | Schauerte |
| 2005/0143785 | A1 | 6/2005 | Libbus |
| 2005/0149127 | A1 | 7/2005 | Libbus |
| 2005/0149128 | A1* | 7/2005 | Heil et al. ............... 607/9 |
| 2005/0149143 | A1 | 7/2005 | Libbus et al. |
| 2005/0149155 | A1 | 7/2005 | Scheiner et al. |
| 2005/0149156 | A1 | 7/2005 | Libbus et al. |
| 2005/0154418 | A1 | 7/2005 | Kieval et al. |
| 2005/0187581 | A1 | 8/2005 | Hara et al. |
| 2005/0187584 | A1 | 8/2005 | Denker et al. |
| 2006/0074453 | A1 | 4/2006 | Kieval et al. |
| 2006/0206159 | A1 | 9/2006 | Moffitt et al. |
| 2006/0217772 | A1 | 9/2006 | Libbus et al. |
| 2006/0229677 | A1 | 10/2006 | Moffitt et al. |
| 2006/0253161 | A1 | 11/2006 | Libbus et al. |
| 2006/0259084 | A1 | 11/2006 | Zhang et al. |
| 2006/0259085 | A1 | 11/2006 | Zhang et al. |
| 2007/0034261 | A1 | 2/2007 | Eichler |
| 2007/0038259 | A1 | 2/2007 | Kieval et al. |
| 2007/0038261 | A1 | 2/2007 | Kieval et al. |
| 2007/0060972 | A1 | 3/2007 | Kieval et al. |
| 2007/0068260 | A1 | 3/2007 | Hong et al. |
| 2007/0088221 | A1 | 4/2007 | Stahmann |
| 2007/0093875 | A1 | 4/2007 | Chavan et al. |
| 2007/0161912 | A1 | 7/2007 | Zhang |
| 2007/0191904 | A1 | 8/2007 | Libbus et al. |
| 2007/0255379 | A1 | 11/2007 | Williams et al. |
| 2007/0260285 | A1 | 11/2007 | Libbus et al. |
| 2009/0228078 | A1 | 9/2009 | Zhang et al. |
| 2010/0076511 | A1 | 3/2010 | Heil, Jr. et al. |
| 2010/0222832 | A1 | 9/2010 | Zhang et al. |
| 2013/0331919 | A1 | 12/2013 | Zhang et al. |

FOREIGN PATENT DOCUMENTS

| | | |
|---|---|---|
| WO | WO-0226314 A1 | 4/2002 |
| WO | WO-03011388 A2 | 2/2003 |
| WO | WO-03082080 A3 | 10/2003 |
| WO | WO-2005065771 A1 | 7/2005 |
| WO | WO-2006115877 A1 | 11/2006 |
| WO | WO-2007050657 A1 | 5/2007 |
| WO | WO-2009075750 A2 | 6/2009 |
| WO | WO-2009075750 A3 | 1/2010 |

OTHER PUBLICATIONS

U.S. Appl. No. 10/745,921, Appeal Brief filed Apr. 23, 2007, 38 pgs.
U.S. Appl. No. 10/745,921, Decision on Appeal mailed Sep. 3, 2008, 18 pgs.
U.S. Appl. No. 10/745,921, Examiner's Answer to Appeal Brief mailed Sep. 27, 2007, 17 pgs.
U.S. Appl. No. 10/745,921, Final Office Action mailed Jan. 14, 2010, 16 pgs.
U.S. Appl. No. 10/745,921, Final Office Action mailed Oct. 25, 2006, 11 pgs.
U.S. Appl. No. 10/745,921, Non Final Office Action mailed Mar. 29, 2006, 10 pgs.
U.S. Appl. No. 10/745,921, Non-Final Office Action mailed Jul. 27, 2009, 15 pgs.
U.S. Appl. No. 10/745,921, Preliminary Amendment filed Feb. 9, 2004, 5 pgs.
U.S. Appl. No. 10/745,921, Reply Brief filed Nov. 27, 2007, 31 pgs.
U.S. Appl. No. 10/745,921, Response filed Jan. 25, 2007 to Final Office Action mailed Oct. 25, 2006, 21 pgs.
U.S. Appl. No. 10/745,921, Response filed Feb. 21, 2006 to Restriction Requirement mailed Jan. 19, 2006, 15 pgs.
U.S. Appl. No. 10/745,921, Response filed May 6, 2009 to Restriction Requirement mailed Jan. 6, 2009, 12 pgs.
U.S. Appl. No. 10/745,921, Response filed Jul. 31, 2006 to Non Final Office Action mailed Mar. 29, 2006, 16 pgs.
U.S. Appl. No. 10/745,921, Response filed Oct. 27, 2009 to Non Final Office Action mailed Jul. 27, 2009, 16 pgs.
U.S. Appl. No. 10/745,921, Restriction Requirement mailed Jan. 6, 2009, 9 pgs.
U.S. Appl. No. 10/745,921, Restriction Requirement mailed Jan. 19, 2006, 5 pgs.
U.S. Appl. No. 10/745,921, Supplemental Preliminary Amendment filed Apr. 25, 2005, 10 pgs.
U.S. Appl. No. 10/745,921, Supplemental Preliminary Amendment filed Sep. 23, 2004, 7 pgs.
U.S. Appl. No. 10/745,925, Notice of Allowance mailed Nov. 14, 2008, 6 pgs.
U.S. Appl. No. 10/746,134, Final Office Action mailed Feb. 21, 2008, 10 pgs.
U.S. Appl. No. 10/746,134, Final Office Action mailed Jul. 10, 2008, 10 pgs.
U.S. Appl. No. 10/746,134, Final Office Action mailed Dec. 26, 2006, 8 pgs.
U.S. Appl. No. 10/746,134, Non Final Office Action mailed May 18, 2007, 12 pgs.
U.S. Appl. No. 10/746,134, Non-Final Office Action mailed Feb. 6, 2009, 10 pgs.
U.S. Appl. No. 10/746,134, Notice of Allowance mailed Aug. 10, 2009, 7 pgs.
U.S. Appl. No. 10/746,134, Preliminary Amendment filed Feb. 9, 2004, 5 pgs.
U.S. Appl. No. 10/746,134, Preliminary Amendment filed Apr. 25, 2005, 8 pgs.

(56) References Cited

OTHER PUBLICATIONS

U.S. Appl. No. 10/746,134, Response filed Feb. 26, 2007 to Final Office Action mailed Dec. 26, 2006, 13 pgs.

U.S. Appl. No. 10/746,134, Response filed Jul. 6, 2009 to Non-Final Office Action mailed Feb. 6, 2009, 16 pgs.

U.S. Appl. No. 10/746,134, Response filed Oct. 5, 2006 to Non Final Office Action mailed May 5, 2006, 16 pgs.

U.S. Appl. No. 10/746,134, Response filed Nov. 19, 2007 to Non-Final Office Action mailed May 18, 2007, 14 pgs.

U.S. Appl. No. 10/746,134, Response filed Dec. 10, 2008 to Final Office Action mailed Jul. 10, 2008, 11 pgs.

U.S. Appl. No. 10/746,134, Supplemental Notice of Allowability mailed Aug. 31, 2009, 5 pgs.

U.S. Appl. No. 10/746,134, Supplemental Preliminary Amendment filed Sep. 23, 2004, 7 pgs.

U.S. Appl. No. 10/746,134, Supplemental Preliminary Amendment filed Nov. 30, 2004, 3 pgs.

U.S. Appl. No. 10/746,852, Advisory Action mailed Jun. 26, 2008, 3 pgs.

U.S. Appl. No. 10/746,852, Appeal Brief filed Dec. 22, 2008, 26 pgs.

U.S. Appl. No. 10/746,852, Decision on Pre-Appeal Brief mailed Aug. 22, 2008, 2 pgs.

U.S. Appl. No. 10/746,852, Examiner's Answer to Appeal Brief mailed Mar. 13, 2009, 17 pgs.

U.S. Appl. No. 10/746,852, Final Office Action mailed Mar. 27, 2008, 15 pgs.

U.S. Appl. No. 10/746,852, Final Office Action mailed Aug. 26, 2008, 14 pgs.

U.S. Appl. No. 10/746,852, Non Final Office Action mailed Apr. 6, 2006, 12 pgs.

U.S. Appl. No. 10/746,852, Non Final Office Action mailed Apr. 17, 2007, 16 pgs.

U.S. Appl. No. 10/746,852, Non Final Office Action mailed Oct. 25, 2006, 15 pgs.

U.S. Appl. No. 10/746,852, Non-Final Office Action mailed Oct. 9, 2007, 15 pgs.

U.S. Appl. No. 10/746,852, Pre-Appeal Brief Request filed Jul. 18, 2008, 5 pgs.

U.S. Appl. No. 10/746,852, Response filed Jan. 9, 2008 to Non-Final Office Action mailed Oct. 9, 2007, 15 pgs.

U.S. Appl. No. 10/746,852, Response filed Jan. 25, 2007 to Non Final Office Action mailed Oct. 25, 2006, 16 pgs.

U.S. Appl. No. 10/746,852, Response filed May 27, 2008 to Final Office Action mailed Mar. 27, 2008, 15 pgs.

U.S. Appl. No. 10/746,852, Response filed Jul. 17, 2007 to Non Final Office Action mailed Apr. 17, 2007, 12 pgs.

U.S. Appl. No. 10/746,852, Response filed Aug. 7, 2006 to Non Final Office Action mailed Apr. 6, 2006, 14 pgs.

U.S. Appl. No. 10/746,861, Advisory Action mailed Jan. 31, 2007, 3 pgs.

U.S. Appl. No. 10/746,861, Advisory Action mailed Jul. 18, 2008, 3 pgs.

U.S. Appl. No. 10/746,861, Decision on Pre-Appeal Brief mailed Nov. 21, 2008, 2 pgs.

U.S. Appl. No. 10/746,861, Examiner Interview Summary mailed Mar. 26, 2010, 3 pgs.

U.S. Appl. No. 10/746,861, Final Office Action mailed Apr. 21, 2008, 13 pgs.

U.S. Appl. No. 10/746,861, Final Office Action mailed Jul. 7, 2010, 12 pgs.

U.S. Appl. No. 10/746,861, Final Office Action mailed Oct. 24, 2006, 20 pgs.

U.S. Appl. No. 10/746,861, Non Final Office Action mailed Apr. 6, 2006, 22 pgs.

U.S. Appl. No. 10/746,861, Non Final Office Action mailed Jul. 12, 2007, 21 pgs.

U.S. Appl. No. 10/746,861, Non-Final Office Action mailed Feb. 2, 2009, 9 pgs.

U.S. Appl. No. 10/746,861, Non-Final Office Action mailed Nov. 24, 2009, 8 pgs.

U.S. Appl. No. 10/746,861, Notice of Appeal filed Apr. 24, 2007, 3 pgs.

U.S. Appl. No. 10/746,861, Pre-Appeal Brief Request for Review filed Oct. 21, 2008, 5 pgs.

U.S. Appl. No. 10/746,861, Response filed Jan. 24, 2007 to Final Office Action mailed Oct. 24, 2006, 12 pgs.

U.S. Appl. No. 10/746,861, Response filed Mar. 24, 2010 to Non-Final Office Action mailed Nov. 24, 2009, 14 pgs.

U.S. Appl. No. 10/746,861, Response filed Jun. 25, 2007 to Advisory Action mailed Jan. 31, 2007 and Final Office Action mailed Oct. 24, 2006, 12 pgs.

U.S. Appl. No. 10/746,861, Response filed Jul. 1, 2009 to Non Final Office Action mailed Feb. 2, 2009, 9 pgs.

U.S. Appl. No. 10/746,861, Response filed Aug. 7, 2006 to Non Final Office Action mailed Apr. 6, 2006, 13 pgs.

U.S. Appl. No. 10/746,861, Response filed Sep. 7, 2010 to Final Office Action mailed Jul. 7, 2010, 13 pgs.

U.S. Appl. No. 10/746,861, Response filed Dec. 12, 2007 to Non-Final Office Action mailed Jul. 12, 2007, 13 pgs.

U.S. Appl. No. 10/746,861, Response filed Jun. 23, 2008 to Final Office Action mailed Apr. 21, 2008, 12 pgs.

U.S. Appl. No. 11/125,997, Non-Final Office Action mailed Sep. 10, 2008, 9 pgs.

U.S. Appl. No. 11/125,997, Response filed May 27, 2008 to Non Final Office Action mailed Feb. 26, 2008, 19 pgs.

U.S. Appl. No. 11/125,997, Response filed Jan. 12, 2009 to Non Final Office Action mailed Sep. 10, 2008, 12 pgs.

U.S. Appl. No. 11/125,997, Advisory Action mailed Jun. 15, 2009, 3 pgs.

U.S. Appl. No. 11/125,997, Final Office Action mailed Mar. 16, 2009, 11 pgs.

U.S. Appl. No. 11/125,997, Non-Final Office Action mailed Feb. 26, 2008, 13 pgs.

U.S. Appl. No. 11/125,997, Notice of Allowance mailed Jan. 28, 2010, 7 pgs.

U.S. Appl. No. 11/125,997, Notice of Allowance mailed Oct. 6, 2009, 6 pgs.

U.S. Appl. No. 11/125,997, Response filed Jul. 16, 2009 to Advisory Action mailed Jun. 15, 2009 and Final Office Action mailed Mar. 16, 2009, 15 pgs.

U.S. Appl. No. 11/125,997, Response filed May 18, 2009 to Final Office Action mailed Mar. 16, 2009, 13 pgs.

U.S. Appl. No. 11/126,097, Final Office Action mailed Feb. 18, 2009, 10 pgs.

U.S. Appl. No. 11/126,097, Non-Final Office Action mailed Aug. 19, 2008, 7 pgs.

U.S. Appl. No. 11/126,097, Notice of Allowance mailed Mar. 24, 2010, 6 pgs.

U.S. Appl. No. 11/126,097, Notice of Allowance mailed Dec. 7, 2009, 7 pgs.

U.S. Appl. No. 11/126,097, Response filed Apr. 28, 2008 to Restriction Requirement mailed Mar. 26, 2008, 13 pgs.

U.S. Appl. No. 11/126,097, Response filed May 4, 2009 to Final Office Action mailed Feb. 18, 2009, 11 pgs.

U.S. Appl. No. 11/126,097, Response filed Jun. 15, 2009 to Restriction Requirement mailed May 14, 2009, 8 pgs.

U.S. Appl. No. 11/126,097, Response filed Nov. 19, 2008 to Non Final Office Action mailed Aug. 19, 2008, 11 pgs.

U.S. Appl. No. 11/126,097, Restriction Requirement mailed Mar. 26, 2008, 9 pgs.

U.S. Appl. No. 11/126,097, Restriction Requirement mailed May 14, 2009, 7 pgs.

U.S. Appl. No. 12/327,601, Non Final Office Action Mailed Dec. 22, 2011, 9 pgs.

U.S. Appl. No. 12/327,601, Response filed Apr. 20, 2012 to Non Final Office Action mailed Dec. 22, 2011, 9 pgs.

U.S. Appl. No. 12/327,601, Response to Restriction Requirement filed Oct. 12, 2011, 11 pgs.

U.S. Appl. No. 12/327,601, Restriction Requirement mailed Sep. 15, 2011, 8 pgs.

U.S. Appl. No. 12/779,177, Response filed Jul. 31, 2012 to Non Final Office Action mailed May 17, 2012, 7 pgs.

(56) References Cited

OTHER PUBLICATIONS

U.S. Appl. No. 12/779,177, Non Final Office Action mailed May 17, 2012, 7 pgs.
U.S. Appl. No. 12/779,177, Notice of Allowance mailed Dec. 10, 2012, 7 pgs.
International Application Serial No. PCT/US2004/043691, International Search Report mailed Mar. 22, 2005, 3 pgs.
International Application Serial No. PCT/US2004/043691, Written Opinion mailed Mar. 22, 2005, 7 pgs.
International Application Serial No. PCT/US2008/013306, Search Report mailed Dec. 1, 2009, 5 pgs.
International Application Serial No. PCT/US2008/013306, Written Opinion mailed Dec. 1, 2009, 8 pgs.
Japanese Application Serial No. 2006-547492, Office Action mailed Jun. 8, 2010, (w/ English Translation), 5 pgs.
Ardell, J. L., et al., "Selective vagal innervation of sinoatrial and atrioventricular nodes in canine heart", Am. J. Physiol. Heart Circ. Physiol., 251(4, Pt 2), (1986), H764-H773.
Bevan, J. A., et al., "Action of lobeline on pulmonary artery mechanoreceptors of the cat", Circ Res., 17, (Jul. 1965), 19-29.
Coleridge, J. C, et al., "Reflex effects of stimulating baroreceptors in the pulmonary artery", J. Physiol, 166, (1963), 197-210.
Kolman, B. S., et al., "The Effect of Vagus Nerve Stimulation Upon Vulnerability of the Canine Ventricle: Role of Sympathetic-Parasympathetic Interactions", Circulation, 52(4), (1975), 578-585.
McMahon, N. C, et al., "Reflex responses from the main pulmonary artery and bifurcation in anaesthetised dogs.", Experimental Physiology, 85(4), (2000), 411-420.
Moore, J. P., et al., "Pulmonary arterial distension and vagal afferent nerve activity in anaesthetized dogs", J Physiol., 555(Pt 3), (Mar. 16, 2004), 805-14.
Murakawa, Y., et al., "Effect of Cervical Vagal Nerve stimulation on Defibrillation Energy: a Possible Adjunct to Efficient Defibrillation", Japanese Heart Journal, 44(1), (Jan. 2003), 91-100.
Nishi, K., et al., "Afferent fibres from pulmonary arterial baroreceptors in the left cardiac sympathetic nerve of the cat", J Physiol., 240(1), (Jul. 1974), 53-66.
Pauza, D. H., et al., "Morphology, distribution, and variability of the epicardiac neural ganglionated subplexuses in the human heart", The Anat. Rec. 259(4), (2000), 353-382.
Schauerte, P. N, et al., "Transvenous parasympathetic cardiac nerve stimulation: an approach for stable sinus rate control", Journal of Cardiovascular Electrophysiology, 10(11), (Nov. 1999), 1517-1524.
Schauerte, P., et al., "Ventricular Rate Control During Atrial Fibrillation by Cardiac Parasympathetic Nerve Stimulation: A Transvenous Approach", J. Am. Coll. Cardiol., 34 (7), (Dec. 1999), 2043-2050.
Scherlag, B. J, et al., "Endovascular stimulation within the left pulmonary artery to induce slowing of heart rate and paroxysmal atrial fibrillation.", Cardiovasc Research, 54(2), (May 2002), 470-475.
U.S. Appl. No. 13/964,807, Advisory Action mailed Sep. 23, 2014, 3 pgs.
U.S. Appl. No. 13/964,807, Response filed Aug. 20, 2014 to Final Office Action mailed Jun. 23, 2014, 15 pgs.
U.S. Appl. No. 13/964,807, Response filed Nov. 24, 2014 to Final Office Action mailed Jun. 23, 2014, 12 pgs.

\* cited by examiner

SYSTEMS FOR USING A PULMONARY ARTERY ELECTRODE

CROSS-REFERENCE TO RELATED APPLICATIONS

This application is a continuation of U.S. application Ser. No. 12/779,177, filed May 13, 2010, now issued as U.S. Pat. No. 8,417,354, which is a continuation of U.S. application Ser. No. 11/125,997, filed May 10, 2005, now issued as U.S. Pat. No. 7,734,348, which is hereby incorporated by reference in its entirety.

The following commonly assigned U.S. patent applications is related, and is herein incorporated by reference in its entirety: "Neural Stimulation System With Pulmonary Artery Lead," Ser. No. 11/126,097, filed on May 10, 2005, now issued as U.S. Pat. No. 7,765,000.

TECHNICAL FIELD

This application relates generally to medical devices and, more particularly, to implantable devices with a pulmonary artery lead.

BACKGROUND

Implantable cardiac devices have been developed in order to treat a number of cardiac disorders. A pacemaker, for example, is a device which paces the heart with timed pacing pulses. A pacemaker can be used to treat bradycardia where the ventricular rate is too slow. Atrio-ventricular conduction defects (i.e., AV block) and sick sinus syndrome represent common causes of bradycardia for which permanent pacing may be indicated. If functioning properly, the pacemaker makes up for the heart's inability to pace itself at an appropriate rhythm to meet metabolic demand by enforcing a minimum heart rate. Implantable devices may also be used to treat cardiac rhythms that are too fast, with either anti-tachycardia pacing or the delivery of electrical shocks to terminate atrial or ventricular tachyarrhythmia/fibrillation.

Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues.

Neural stimulation has been the subject of a number of studies and has been proposed for several therapies. The autonomic system controls physiological activities of the body and the imbalance of autonomic tone is related to many diseases and conditions. Vagus nerve stimulation has been proposed to treat sleep disorders, gastrointestinal motility, eating disorders, obesity, anorexia, gastrointestinal tract disorders, hypertension, coma, and epilepsy. Direct electrical stimulation of parasympathetic nerves can activate the baroreflex, inducing a reduction of sympathetic nerve activity and reducing blood pressure by decreasing vascular resistance. In a CHF patient, the patient's sympathetic tone increases and catecholamine increase, causing sudden cardiac death. Vagus nerve stimulation may antagonize sympathetic tone, and may prevent sudden cardiac death. The vagal stimulation counteracts the high sympathetic tone associated with CHF, resulting in a decreased heart rate, reduced oxygen demand, increased diastolic period, and reduced incidence of ventricular arrhythmia. A decrease in the sympathetic tone decreases the excitability of the heart, which decreases arrhythmias. Modulation of the sympathetic and parasympathetic nervous system with neural stimulation has been shown to have positive clinical benefits, such as protecting the myocardium from further remodeling and predisposition to fatal arrhythmias following a myocardial infarction.

SUMMARY

Various embodiments relate of the present subject matter to a method. According to various method embodiments, at least one electrode is positioned in a right pulmonary artery and at least one electrode is positioned in a left pulmonary artery. Stimulation is applied using at least one of the electrodes.

Various embodiments of the present subject matter relate to a lead. Various lead embodiments comprise a lead body including a first portion, a first branch and a second branch. The first portion has an end adapted to connect to an implantable medical device. The first branch and the second branch is connected to the first portion at a bifurcated region. The first branch includes a distal end adapted to be fed into a right pulmonary artery and to securely position at least one electrode within the right pulmonary artery. The second branch includes a distal end adapted to be fed into a left pulmonary artery and to securely position at least one electrode within the left pulmonary artery.

Various embodiments of the present subject matter relate to an implantable medical device. Various device embodiments include at least one lead adapted to extend through a pulmonary valve to securely position at least one electrode within a right pulmonary artery and at least one electrode within a left pulmonary artery. Stimulation circuitry is connected to the at least one lead to apply stimulation to at least one of the electrodes. A controller is connected to the stimulation circuitry to control application of the stimulation.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
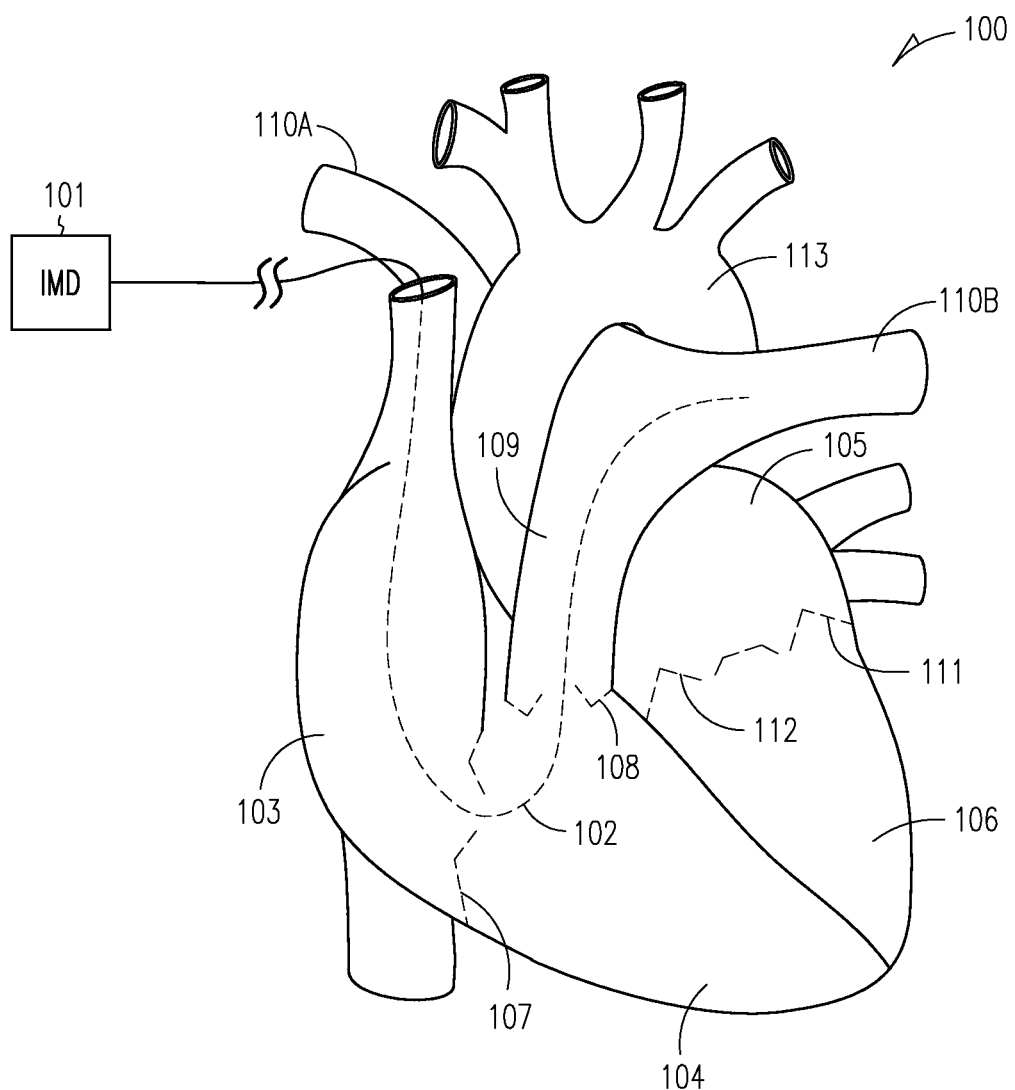
FIG. 1 illustrates a heart, and an implantable medical device (IMD) embodiment with a pulmonary artery lead.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter generally relates to systems, devices, leads and methods to provide stimulation using electrode(s) positioned within the pulmonary artery. The left and right pulmonary arteries are proximate to the left and right atria, respectively, and are proximate to branches of the vagus nerve. The vagus nerve includes a left and right vagus nerve. The right vagus nerve passes anterior to the subclavian artery, breaks up into pulmonary plexus posterior to root of the right lung, refers and then breaks up into esophageal and cardiac plexuses. The left vagus nerve passes to the left of the aortic arch and posterior to the root of the left lung, giving pulmonary, esophageal and cardiac plexuses. Thus, pulmonary artery lead(s) can provide electrode(s) within the right pulmonary artery to capture right atrial tissue and/or to depolarize right vagal nerve fibers, and can provide electrode(s) within the left pulmonary artery to capture left atrial tissue and/or to depolarize left vagal nerve fibers. The pulmonary artery lead(s) provide minimally-invasive means to provide vagal stimulation.

Embodiments of the present subject matter use pulmonary artery lead(s) to perform atrial rhythm management activities or functions. Examples of atrial rhythm management activities include sensing atrial events and capturing atrial tissue. An example of sensing involves sensing a p-wave, allowing the delivery of vagal stimulation to occur with or near the p-wave. Examples of capturing atrial tissue include pacing atrial tissue and shocking atrial tissue as part of a therapy for atrial tachycardia or fibrillation.

Some embodiments provide both neural stimulation to a vagus nerve target and atrial rhythm management activities using pulmonary artery lead(s). Some embodiments provide at least one electrode in a right pulmonary artery and at least one electrode in a left pulmonary artery using at least one pulmonary artery lead. These electrodes are capable of being used to stimulate left and/or right vagus nerve targets, to capture left and/or right atrial tissue, and to provide various combinations of left/right vagal stimulation and capture of left/right atrial tissue.

Some lead embodiments include a pre-formed pulmonary artery pacing lead, some include a pre-formed bifurcated pulmonary artery lead with a left pulmonary artery branch and a right pulmonary artery branch, and some include a stent-like pulmonary artery pacing lead. These pre-formed lead embodiments are adapted to passively fixate the lead in the pulmonary artery. Active fixation may also be used.

The pulmonary artery lead system provided herein can be used in a number of therapies. Some embodiments integrate vagus nerve stimulation with pacing and shocking for a variety of therapeutic purposes. Some embodiments apply direct and targeted vagus nerve stimulation through the stimulation of specific parasympathetic efferent nerve branch compared to a more general inhibition of sympathetic activity. The direct and targeted vagus nerve stimulation can reduce or minimize side effects and avoid interfering with other systems/organs.

Pulmonary artery leads are capable of neural stimulation, and in some embodiments, cardiac pacing or shocking can be used within a variety of cardiac rhythm management (CRM) therapies for bi-atrial pacing, synchronized and more effective pacing, reduction of atrial fibrillation (AF) or atrial tachycardia (AT) shocking threshold, reduction of defibrillation threshold, prevention and treatment of AF/AT, cardiac heart failure therapy (CHF), and prevention of sudden cardiac death (SCD) if applied with shocking electrodes. Some embodiments stimulate the left vagus nerve for AF therapy, possibly with a left atrium shocking electrode in the pulmonary artery. In a CHF patient, the patient's sympathetic tone increases and catecholamine increase, causing sudden cardiac death. Vagus nerve stimulation may antagonize sympathetic tone, and may prevent sudden cardiac death. Some embodiments integrate vagus nerve stimulation from within the pulmonary artery with right ventricle shocking system (tachy lead system) to reduce defibrillation threshold.

One therapy example to treat cardiac heart failure (CHF) applies vagus stimulation within the right pulmonary artery, the left pulmonary or both the right and left pulmonary arteries in conjunction with a cardiac resynchronization therapy (CRT), which is associated with autonomic imbalance. CRT therapy may involve biventricular pacing and/or biatrial pacing. The vagal stimulation counteracts the high sympathetic tone associated with CHF, resulting in a decreased heart rate, reduced oxygen demand, increased diastolic period, and reduced incidence of ventricular arrhythmia. A therapy example to reduce a defibrillation threshold applies vagus stimulation within the right pulmonary artery, the left pulmonary or both the right and left pulmonary arteries in anticipation of a subsequent defibrillation or anti-tachycardia shock. A therapy example to prevent atrial fibrillation applies vagus stimulation within the left pulmonary artery in conjunction with biatrial pacing using electrodes within the right and left pulmonary arteries. A lead positioned in the left pulmonary artery is used to stimulate the left vagus. The left vagus stimulation can also depolarize the left atrium. This therapy example is capable of reducing AF burden. A therapy example applies vagus stimulation within the right pulmonary artery, the left pulmonary or both the right and left pulmonary arteries to compensate for pace-induced nerve sprouting. The pacing of the left and/or right vagus nerve targets increase local sympathetic innervation and provide heterogeneity of the cardiac refractory period. The vagus stimulation counterbalances the effects of pace-induced nerve sprouting, reducing ventricular arrhythmia and AF burden.

According to a system embodiment, a lead is fed through a right pulmonary artery and is used to stimulate the right vagus nerve and to provide right atrial pacing. The stimulation of the vagus nerve is synchronized with the p-wave and/or right atrial pacing. In addition to pacing the right atrium, some embodiments stimulate the left vagus nerve via the left pulmonary artery. The vagus nerve stimulation via the left pulmonary artery has the potential to capture the left atrium, too. Some embodiments provide a bi-atrial pacing configuration using vagus nerve stimulation from the left pulmonary artery along with the pacing of the right atrium from the right pulmonary artery. Such bi-atrial pacing could reduce atrial fibrillation burden. Some embodiments simultaneously stimulate the left and right vagus nerves via the left pulmonary artery and the right pulmonary artery and pace the right atrium from the right pulmonary artery.

According to some system embodiments to treat heart failure, vagus nerve stimulation is integrated in cardiac resynchronization therapy (CRT) applications. In some embodiments, a right atrium lead is positioned to be able to capture the right atrium and to sense intrinsic electrical activity of the right atrium, and a right ventricular lead is positioned to be able to capture the right ventricle and to sense intrinsic electrical activity of the right ventricle. The left ventricle can be paced and intrinsic electrical activity of the left ventricle can be sensed using a lead fed through a coronary vein or using an epicardial lead. Neural stimulation is provided through a lead fed into the pulmonary artery to stimulate the left pulmonary artery and/or the right pulmonary artery. For a heart failure patient, stimulation of the vagus nerve may antagonize the sympathetic role to reduce ventricular arrhythmia and reduce oxygen consumption of the heart.

In a system embodiment to provide atrial fibrillation therapy, at least one electrode is provided in the left pulmonary artery to stimulate the left vagus nerve and for use to shock the left atrium. This has the potential to reduce atrial shocking threshold and mitigate pain of the patient caused by shocks to terminate atrial fibrillation and atrial tachycardia. In some embodiments, such a system with electrode(s) in the pulmonary artery can be used without or independent of other defibrillation systems, such as a system that includes an electrode within a right atrium, an electrode in a right ventricle, and a device housing (also referred to as a can) positioned to create electrical vectors across the left atrium. In some embodiments, such a system with electrode(s) in the pulmonary artery can be used with other defibrillation systems, such as a system that provides stimulation vectors across the atrium between electrodes in the right atrium the right ventricle, and a can. A multi-electrode lead can be used, with a spiral shaped electrode in the pulmonary artery.

In a system embodiment to treat sudden cardiac death (SCD), a pulmonary artery lead is used in conjunction with a tachy lead system. The pulmonary artery lead is used to stimulate a vagus nerve to reduce a defibrillation threshold (DFT) for the tachy lead system.

Illustrated IMD and Pulmonary Artery Lead Embodiments

FIG. 1 illustrates a heart 100, and an implantable medical device (IMD) embodiment 101 with a pulmonary artery lead 102. The illustrated heart 100 includes a right atrium 103, a right ventricle 104, a left atrium 105 and a left ventricle 106. The right atrium 103 and right ventricle is separated by a tricuspid valve 107. Blood flows from the right atrium 103, through a tricuspid valve 107, into the right ventricle 104, through a pulmonary valve 108 and into a pulmonary artery 109. The blood flows to the lungs through right and left pulmonary arteries 110A and 110B, and returns to the left atrium 105 from the lungs through pulmonary veins, not shown in the figure. The blood flows from the left atrium 105, through a mitral valve 111 into a left ventricle, and through the aortic valve 112 into the aorta 113 for distribution throughout the body. The illustrated lead 102 includes a break, right before entering the heart, to illustrate that illustration is not drawn to scale and to illustrate that the placement of the IMD 101 can vary. The stimulation electrode(s) are not in direct neural contact with the parasympathetic nerve when a transvascular neural stimulation approach is used. Thus, problems associated with neural inflammation and injury commonly associated with direct contact electrodes are reduced.

FIGS. 2A-2D illustrate various embodiments of pulmonary artery lead(s) to position electrode(s) in left and/or right pulmonary arteries. Various numbers of electrodes can be positioned within each pulmonary artery. Additionally, various types of electrodes can be used, including tip and ring electrodes, coil electrodes such as can be used for defibrillation shocks, and expandable stent-like electrodes. Some leads are configured to provide bipolar stimulation (e.g. stimulation vector between ring and electrode) and some leads are configured to provide unipolar stimulation (e.g. stimulation vector between electrode on lead and another electrode on another lead or a conductive housing). Various lead embodiments are pre-formed to appropriately abut against a wall of the pulmonary artery and passively fixate the lead therein. Active fixation may also be used.

Figure 2A:
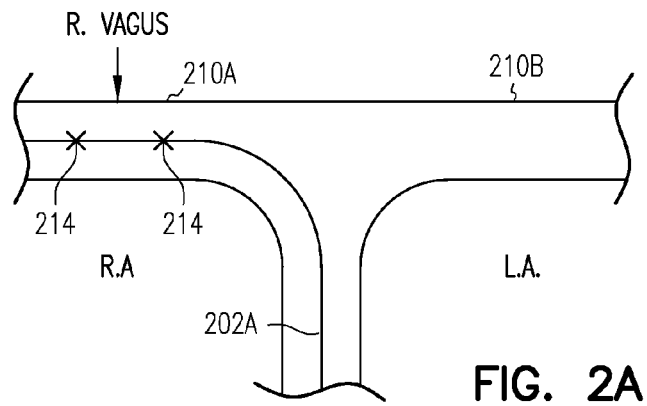
FIGS. 2A-2D illustrate various embodiments of pulmonary artery lead(s) to position electrode(s) in left and/or right pulmonary arteries.

FIG. 2A illustrates a pulmonary artery lead 202A, such as the lead 102 illustrated in FIG. 1, adapted to be fed in the right pulmonary artery 210A. Two electrodes 214 are illustrated. In some embodiments, at least one of the electrodes is configured and positioned to elicit depolarization of the right vagus nerve; and in some embodiments, at least one of the electrodes is configured and positioned to capture atrial tissue and/or sense atrial intrinsic events from the right atrium. Some embodiments use a single electrode or common electrodes on the lead to provide the neural stimulation and the capture and sensing functions associated with atrial rhythm management.

Figure 2B:
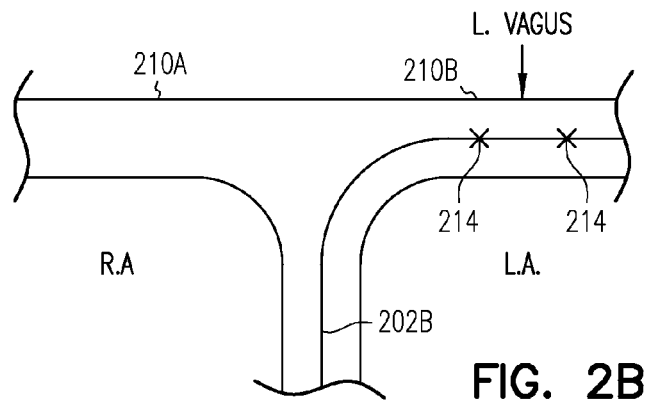

FIG. 2B illustrates a pulmonary artery lead 202B, such as the lead 102 illustrated in FIG. 1, adapted to be fed in the left pulmonary artery 210B. Two electrodes 214 are illustrated. In some embodiments, at least one of the electrodes is configured and positioned to elicit depolarization of the left vagus nerve; and in at least some embodiments, at least one of the electrodes is configured and positioned to capture atrial tissue and/or sense atrial intrinsic events from the left atrium. Some embodiments use a single electrode or common electrodes on the lead to provide the neural stimulation and the capture and sensing functions associated with atrial rhythm management.

The right vagal branch, the left vagal branch or a combination of the right and left vagal branches are capable of being stimulated. The left and right vagal branches innervate different areas of the heart, and thus provide different results when stimulated. According to present knowledge, the right vagus nerve appears to innervate the right side of the heart, including the right atrium and right ventricle, and the left vagus nerve appears to innervate the left side of the heart, including the left atrium and left ventricle. Stimulation of the right vagus has more chronotropic effects because the sinus node is on the right side of the heart. Thus, various embodiments selectively stimulate the right vagus nerve and/or the left vagus nerve to selectively control contractility, excitability, and inflammatory response on the right and/or left side of the heart.

Figure 2C:
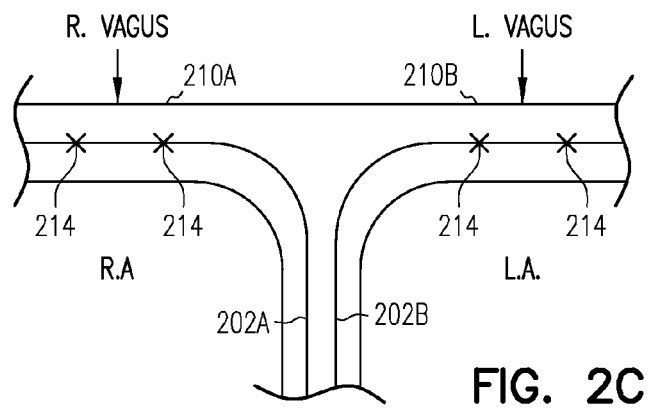
Figure 2D:
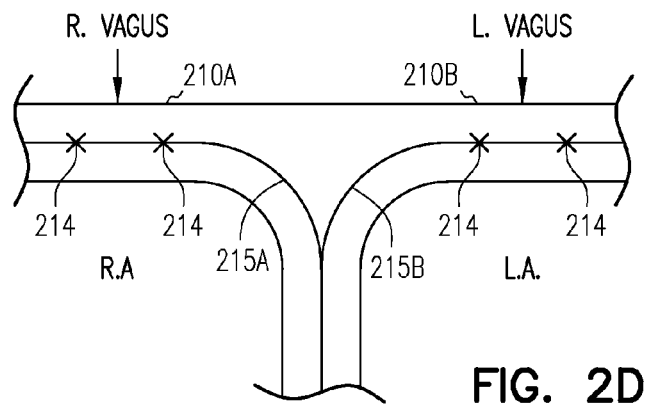

FIG. 2C illustrates a first pulmonary artery lead 202A adapted to be fed through a pulmonary valve and secured within a right pulmonary artery 210A, and a second pulmonary artery lead 202B adapted to be fed through a pulmonary valve and secured within a left pulmonary artery 210B. The electrodes 214 can be configured and positioned for use in stimulating the right and/or left vagus nerve and for use in capturing atrial tissue or sensing atrial events in the right and/or left atrium. FIG. 2D illustrates a bifurcated pulmonary artery lead with a right pulmonary artery branch 215A to securely position at least one electrode 214 in the right pulmonary artery, and a left pulmonary artery branch 215B to securely position at least one electrode 214 within the left pulmonary artery. The electrodes can have dedicated conductors leading back to the controller for independent operation, or two or more conductors can share a conductor to provide a common electrical connection between the controller and the electrodes.

Figure 3:
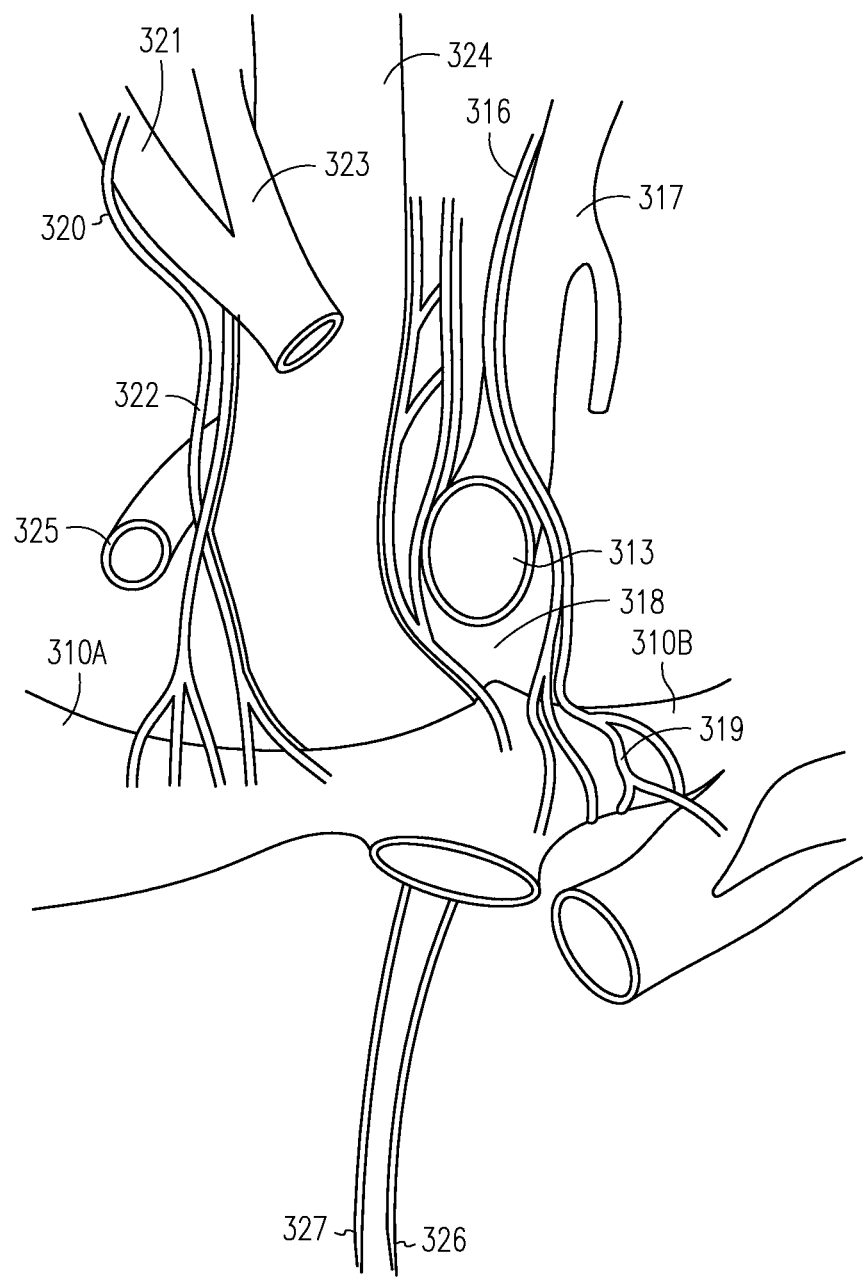
FIG. 3 illustrates physiology of the left and right pulmonary arteries and the left and right vagus nerves.

FIG. 3 illustrates physiology of the left and right pulmonary arteries and the left and right vagus nerves. A left vagus nerve 316 extends next to a subclavian artery 317. Various nerves extend around the arch of the aorta 313. Vagus nerve 316 also extends past the ligamentum arteriosum 318. The anterior pulmonary plexus 319 crosses the left pulmonary artery 310B. Right vagus nerve 320 extends past a subclavian artery 321. Cardiac nerves 322 extend past the brachiocephalic trunk 323 near the trachea 324. Cardiac nerves 322 also extend past the arch of an azygos vein 325 to the right pulmonary artery 310A. A lower portion 326 of the left vagus nerve 316 and a lower portion 327 of the right vagus nerve 320 appear in the lower portion of FIG. 3.

Illustrated Device Embodiments

Figure 4:
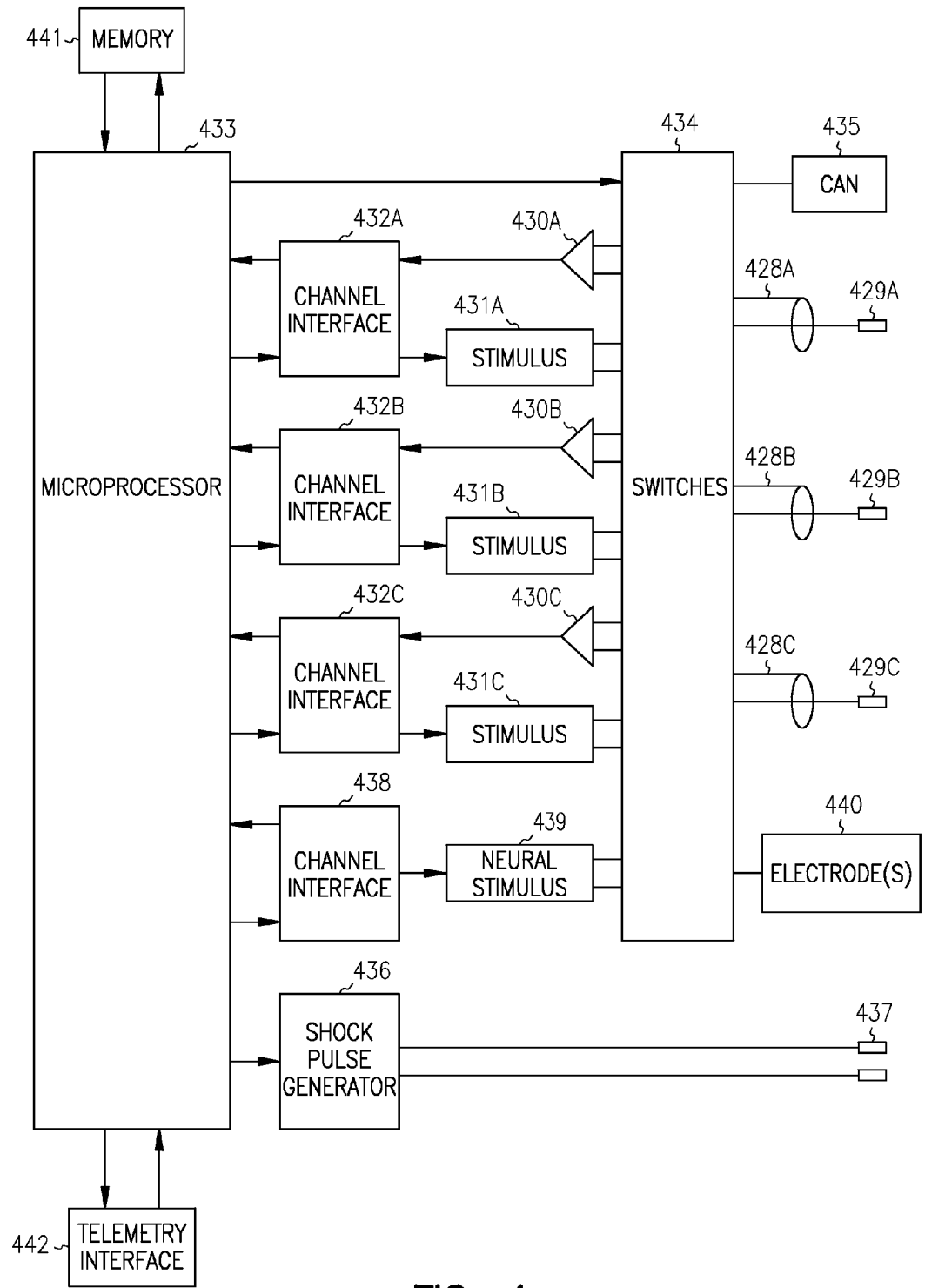
FIG. 4 illustrates a system diagram of an implantable medical device embodiment configured for multi-site stimulation and sensing.

FIG. 4 illustrates a system diagram of an implantable medical device embodiment configured for multi-site stimulation and sensing. Pacing, as used in the discussion of this figure, relates to electrical stimulation. In various embodiments, the stimulation for a given channel includes stimulation to capture myocardia, neural stimulation or both pacing and neural stimulation. In embodiments in which a channel is used to selectively provide both pacing and neural stimulation, the parameters of the stimulation signal, such as amplitude and frequency, are adjusted to provide myocardial pacing without neural stimulation, neural stimulation without myocardial pacing, or both myocardial pacing and neural stimulation. Three illustrated sensing and pacing channels, designated "A" through "C," comprise bipolar leads with ring electrodes 428A-C and tip electrodes 429A-C, sensing amplifiers 430A-C, pulse generators 431A-C, and channel interfaces 432A-C. Each of these channels thus includes a stimulation channel extending between the pulse generator and the electrode and a sensing channel extending between the sense amplifier and the electrode. The channel interfaces 432A-C communicate bidirectionally with microprocessor 433, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry detects a chamber sense, either an atrial sense or ventricular sense, when an electrogram signal (i.e., a voltage sensed by an electrode representing cardiac electrical activity) generated by a particular channel exceeds a specified detection threshold. Algorithms used in particular stimulation modes employ such senses to trigger or inhibit stimulation, and the intrinsic atrial and/or ventricular rates can be detected by measuring the time intervals between atrial and ventricular senses, respectively. The AV conduction can be measured by measuring a time interval between atrial and ventricular intrinsic events. According to various embodiments, the pulse generator is adapted to vary parameters of a neural stimulation signal, such as amplitude, frequency and duty cycle, for example.

The switching network 434 is used to switch the electrodes to the input of a sense amplifier in order to detect intrinsic cardiac activity and to the output of a pulse generator in order to deliver stimulation. The switching network also enables the device to sense or stimulate either in a bipolar mode using both the ring and tip electrodes of a lead or in a unipolar mode using only one of the electrodes of the lead with the device housing or can 435 serving as a ground electrode or another electrode on another lead serving as the ground electrode. A shock pulse generator 436 is also interfaced to the controller for delivering a defibrillation shock via a pair of shock electrodes 437 to the atria or ventricles upon detection of a shockable tachyarrhythmia. Channel interface 438 and neural stimulation generator 439 provide a connection between the microprocessor and the switch to deliver neural stimulation pulses to neural stimulation electrode(s) 440. Various pulmonary lead embodiments include one or more of electrodes 428A-C, 429A-C, 437 and 440. These electrodes can also be provided on other leads.

The controller or microprocessor controls the overall operation of the device in accordance with programmed instructions stored in memory 441, including controlling the delivery of stimulation via the channels, interpreting sense signals received from the sensing channels, and implementing timers for defining escape intervals and sensory refractory periods. The controller is capable of operating the device in a number of programmed stimulation modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse Inhibited stimulation modes utilize escape intervals to control pacing in accordance with sensed intrinsic activity such that a stimulation pulse is delivered to a heart chamber during a cardiac cycle only after expiration of a defined escape interval during which no intrinsic beat by the chamber is detected. Escape intervals for ventricular stimulation can be restarted by ventricular or atrial events, the latter allowing the pacing to track intrinsic atrial beats. A telemetry interface 442 is also provided which enables the controller to communicate with an external programmer or remote monitor. Some embodiments incorporate sensor channels into the device for receiving signals indicative of sense physiological parameters, such as parameters indicative of contractility, AV conduction and/or sinus rate.

Figure 5:
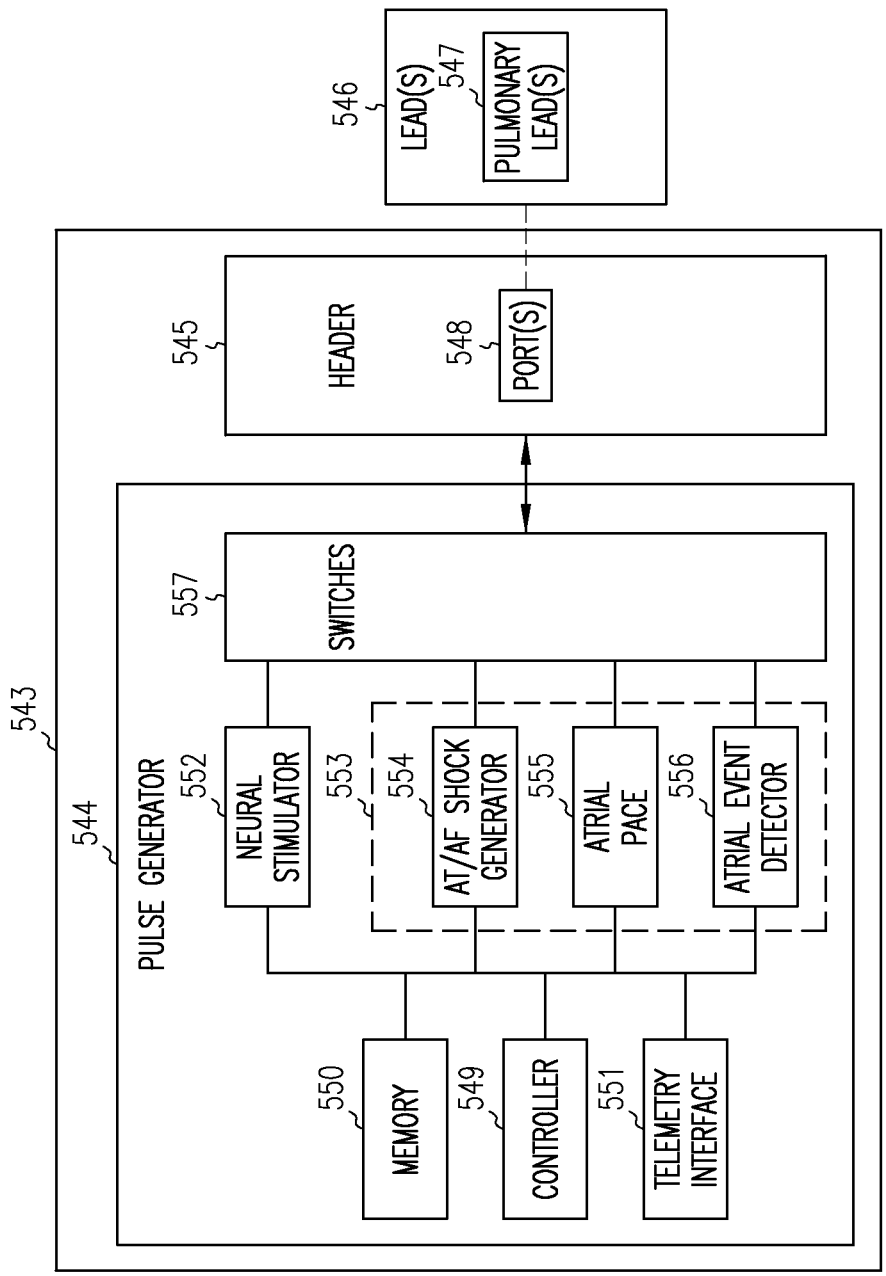
FIG. 5 illustrates a system diagram of an implantable medical device embodiment with function modules shown to provide neural stimulation and atrial rhythm management functions.

FIG. 5 illustrates a system diagram of an implantable medical device embodiment with function modules shown to provide neural stimulation and atrial rhythm management functions. The illustrated device 543 generally includes a pulse generator 544 and a header 545. Lead(s) 546, including pulmonary artery lead(s) 547, are capable of being connected to the illustrated device 543 via port(s) 548 in the header 545. The illustrated pulse generator 544 includes a controller 549 and a memory 550 connected to the controller. The memory includes computer-readable instructions and data which, when operated on by the controller, are used to perform the functions, including the neural stimulation and atrial rhythm management functions, of the device. A telemetry interface 551 is also illustrated, allowing an implanted device 543 to wirelessly communicate with an external device such as a programmer or a patient's computer or portable electronic device. A neural stimulator module 552 is connected to the controller 549, both of which cooperate to provide neural stimulation to desired neural stimulation targets using at least one of the lead(s) 546. For example, one or more pulmonary artery leads can be used to transvascularly deliver vagal stimulation to a right and/or left vagus nerve. The dotted lines generally illustrate modules considered herein to be examples of atrial rhythm management modules 553. A shock generator 554 is connected to the controller 549, both of which cooperate to treat atrial tachycardia and/or atrial fibrillation by shocking atrial tissue using at least one lead 546. An atrial pace module 555 is connected to the controller 549, both of which cooperate to pace atrial tissue using at least one lead 546 to provide a desired atrial rhythm. An atrial event detector 556 is connected to the controller 549, both of which cooperate to be capable of sensing atrial electrical events, including intrinsic and paced events. The modules 552, 554, 555, 556 are connected to the desired electrode(s) on the desired lead(s) by switches 557 that provide desired channels between the port(s) 548 and the modules 552, 554, 555 and 556.

Illustrated Therapy Embodiments

Figure 6:
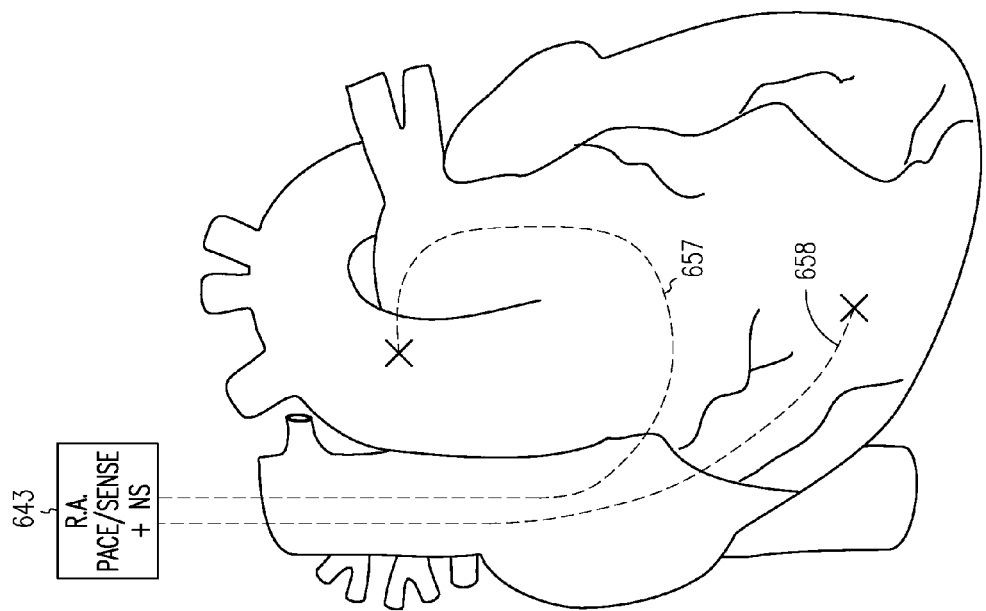
FIG. 6 illustrates an implantable medical device (IMD) embodiment with a right pulmonary artery lead and a right ventricle lead.

FIG. 6 illustrates an implantable medical device (IMD) embodiment 643 with a right pulmonary artery lead 657 and a right ventricle lead 658. The illustrated IMD 643 is capable of performing right atrial pacing and sensing and performing neural stimulation of a right vagus nerve target using electrode(s) on the right pulmonary artery lead 657. According to some embodiments, the same stimulation signal and the same electrode(s) on the right pulmonary artery lead is (are) used to pace the right atrium and to stimulate the right vagus nerve. Atrial events can be sensed from the same electrode(s) on the right pulmonary artery lead. Neural stimulation can be synchronized with sensed p-waves to avoid unintentionally capturing the right atrium during the neural stimulation. Some embodiments use electrode(s) specifically configured and positioned to stimulate a neural target of the right vagus nerve and to use electrode(s) specifically configured and positioned to capture right atrial tissue. Some embodiments control signal parameters, such as amplitude and frequency, of the stimulation signal to control whether the stimulation signal depolarizes a neural pathway and/or captures atrial tissue. An application for the illustrated IMD 643 includes vagal stimulation with the ability to synchronize the vagal stimulation to refractory periods associated with paced or intrinsic atrial events to avoid unintentional atrial capture caused by the vagal stimulation.

Figure 7:
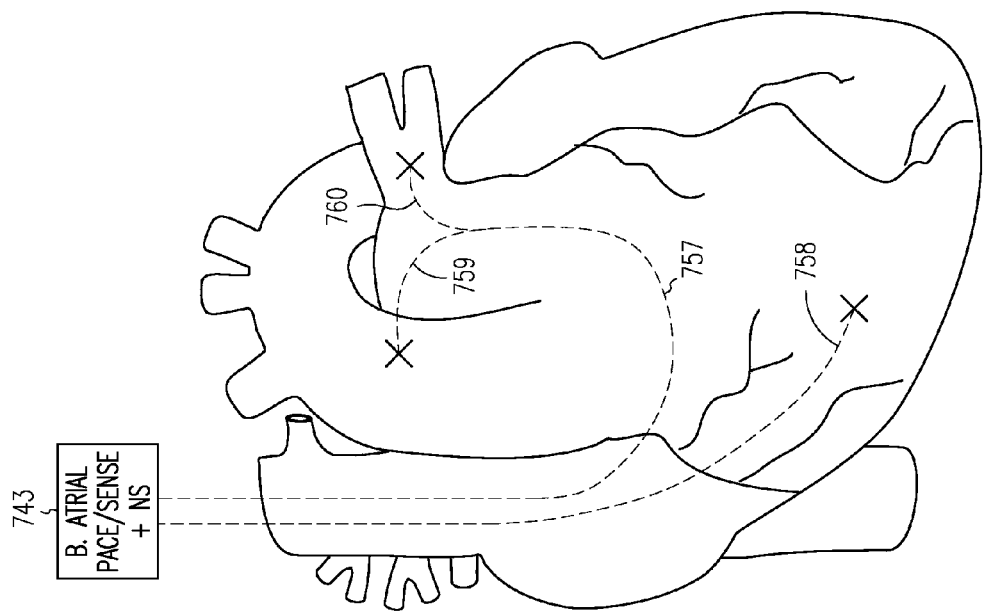
FIG. 7 illustrates an implantable medical device (IMD) embodiment with a bifurcated pulmonary artery lead having distal branches extending into a right pulmonary artery and a left pulmonary artery, and with a right ventricle lead.

FIG. 7 illustrates an implantable medical device (IMD) embodiment 743 with a bifurcated pulmonary artery lead 757 having distal branches 759 and 760 extending into a right pulmonary artery and a left pulmonary artery, and with a right ventricle lead 758. The illustrated IMD 743 is capable of performing biatrial pacing using the distal branches 759 and 760 of the pulmonary artery lead(s) 757. The illustrated lead is a bifurcated lead. Two leads can be used in place of the bifurcated lead. The illustrated IMD is also capable of sensing atrial events using electrode(s) the right and/or left pulmonary arteries, pacing or defibrillating atrial tissue using electrode(s) in the right and/or left pulmonary arteries, and/or providing neural stimulation of the right and/or left vagus nerve target. Various embodiments use different configurations for sensing, capturing atrial tissue and stimulating vagal nerves. According to some embodiments, the same stimulation signal and the same electrode(s) on the distal branches 759 and 760 is (are) used to pace atrial tissue and to stimulate the corresponding vagus nerve. Atrial events can be sensed from the same electrode(s). Neural stimulation can be timed based on sensed p-waves to avoid unintentionally capturing atrial tissue. Some embodiments use electrode(s) specifically configured and positioned to stimulate a neural target of the right vagus nerve and to use electrode(s) specifically configured and positioned to capture right atrial tissue. Some embodiments control signal parameters, such as amplitude and frequency, of the stimulation signal to control whether the stimulation signal depolarizes a neural pathway and/or captures atrial tissue. An application for the illustrated IMD 743 includes synchronized biatrial pacing for a resynchronization therapy for a heart failure patient who has uncoordinated atrial contractions. Additional leads can be used to pace the right and left ventricles to provide coordinated pacing for each chamber of the heart.

Figure 8:
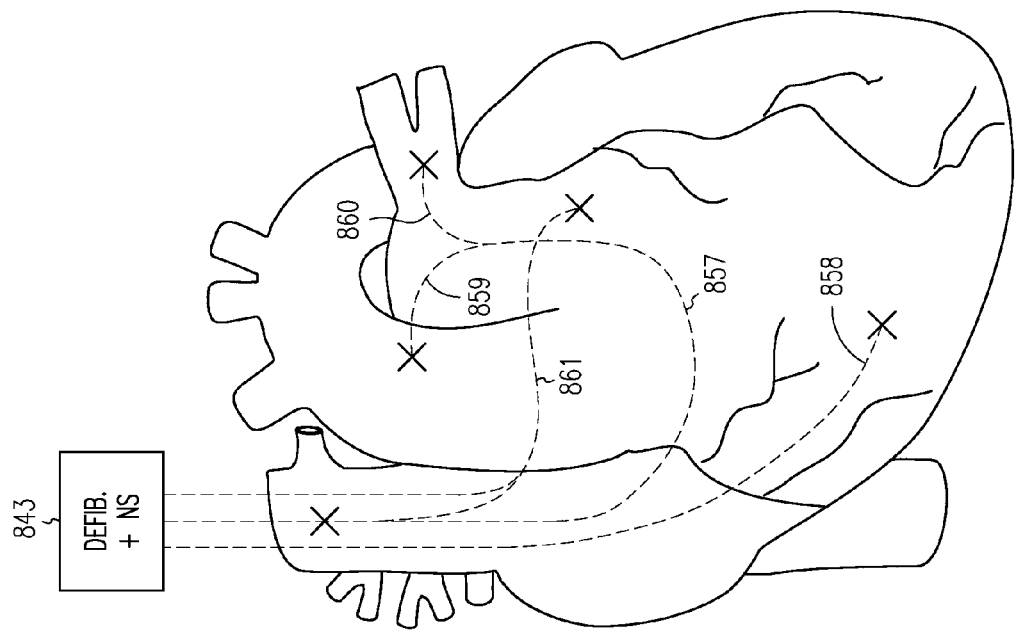
FIG. 8 illustrates an implantable medical device (IMD) embodiment capable of providing atrial defibrillation therapy integrated with vagal stimulation.

FIG. 8 illustrates an implantable medical device (IMD) embodiment 843 capable of providing atrial defibrillation therapy integrated with vagal stimulation. The illustrated IMD includes a pulmonary artery lead 857, a right ventricle lead 858, and a coronary sinus lead 861. The illustrated pulmonary artery lead 857 includes a right pulmonary artery branch 859 and a left pulmonary artery branch 860. The illustrated IMD is capable of providing an atrial shock using a variety of configurations, and is also capable of stimulating vagal nerves. Potential benefits of stimulating vagal cardiac nerves include reducing inflammatory response following myocardial infarction, and reducing the electrical stimulation threshold for defibrillating. For example, when a tachycardia is sensed, vagal nerve stimulation is applied, and then a defibrillation shock is applied. The vagal nerve stimulation allows the defibrillation shock to be applied at less energy.

The illustrated right ventricle lead 858 is an endocardial bi-polar lead with electrodes arranged for establishing electrical contact with the right ventricle of the heart. These electrodes permit bi-polar sensing of ventricular activations in the right ventricle. The illustrated lead 858 is fed through the superior vena cava, into the right atrium and then into the right ventricle.

The illustrated coronary sinus lead 861 is an atrial shocking lead, generally including a first or tip electrode and a second or proximal electrode. Additional electrodes can be incorporated on the lead 861. Such electrodes may be useful in placing the lead by providing various potential electrode configurations for use in providing the desired sensing and stimulating functions. The coronary sinus lead 861 is flexible and arranged to be passed down the superior vena cava, into the right atrium, into the coronary sinus ostium, and advanced into the coronary sinus channel of the heart near the left side thereof so that the first or tip electrode is within the coronary sinus channel either within the coronary sinus adjacent the left ventricle and beneath the left atrium or within the great cardiac vein adjacent the left ventricle and beneath the left atrium. The electrodes are spaced apart such that when the first electrode is positioned as described above, the second electrode is in the right atrium. The electrodes on the coronary sinus lead 861 are capable of providing bi-polar sensing of heart activity in the atria, and further are capable of delivering defibrillating or cardioverting electrical energy to the atria. Defibrillating energy can also be applied between the can or housing of the IMD 843 and other electrode(s) on the right ventricle lead 858 and the coronary sinus lead 861. The branches 859 and 860 of the pulmonary artery lead 857 can be used with the coronary sinus lead 857 and right ventricle lead 858. The electrodes on the branches 859 and 860 can be positioned and configured to provide targeted vagal stimulation of a particular vagal pathway, to be used in sensing left and/or right atrial activity, and/or to be used to capture right and/or left atrial tissue. The electrodes on the branches 859 and 860 can be used with a conductive housing on the IMD 843 or with other electrodes on other leads, such as the coronary sinus lead 861, to provide desired sensing, pacing and shocking vectors. The branches 859 and 860 of the pulmonary artery lead 857 can be used independent of the coronary sinus lead 857 and right ventricle lead 858. Electrodes on the branches can provide vagal stimulation, along appropriate sensing, pacing and shocking vectors using other electrodes on the branches or a conductive housing of the IMD.

Figure 9:
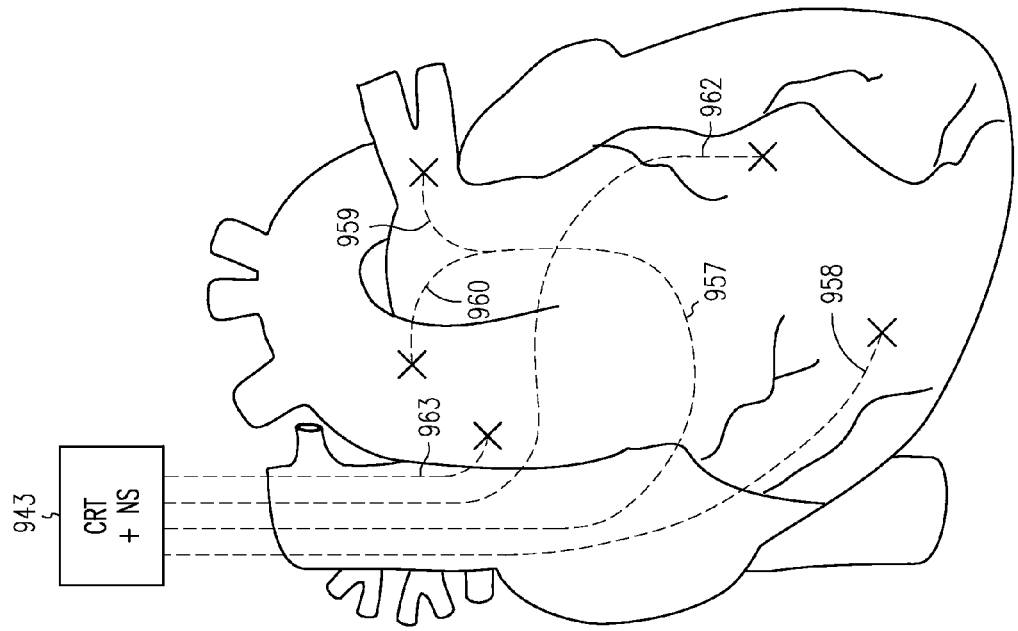
FIG. 9 illustrates an implantable medical device (IMD) embodiment capable of providing cardiac resynchronization therapy (CRT) integrated with vagal stimulation.

FIG. 9 illustrates an implantable medical device (IMD) embodiment 943 capable of providing cardiac resynchronization therapy (CRT) integrated with vagal stimulation. The illustrated IMD includes a pulmonary artery lead 957 with a right pulmonary artery branch 959 and a left pulmonary artery branch 960, a left ventricle lead 962 extending through the coronary sinus, a right ventricle lead 958, and a right atrial lead 963. The illustrated left ventricle lead 962 is fed through the coronary sinus and further advanced into branch veins. Various embodiments of the illustrated device is capable of providing vagal stimulation along with biventricular pacing and/or biatrial pacing to provide resynchronization therapy. Some embodiments provide biatrial pacing using electrodes in the right and left pulmonary arteries. The synchronization provided by biatrial pacing can reduce an atrial tachycardia and atrial fibrillation burden, such as a reentry tachycardia.

CRT devices affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. A common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace. CRT can also involve bi-atrial pacing.

CRT can be beneficial in reducing the deleterious ventricular remodeling which can occur in post-MI and heart failure patients. Presumably, this occurs as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle in a manner which causes a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

Activity of the autonomic nervous system is at least partly responsible for the ventricular remodeling which occurs as a consequence of an MI or due to heart failure. Remodeling can be affected by pharmacological intervention with the use of, for example, ACE inhibitors and beta-blockers. Pharmacological treatment carries with it the risk of side effects, however, and it is also difficult to modulate the effects of drugs in a precise manner. The present subject matter employs electrostimulatory means to modulate autonomic activity. When delivered in conjunction with ventricular resynchronization pacing, such modulation of autonomic activity acts synergistically to reverse or prevent cardiac remodeling.

In various embodiments, a neural stimulation channel uses a lead adapted to be intravascularly disposed within a pulmonary artery to stimulate an appropriate nerve, e.g., near a baroreceptor in the case of a sympathetic inhibition channel or near a parasympathetic nerve in the case of a parasympathetic stimulation channel. Some CRT devices include lead(s) to pace and/or sense the right atrium and/or lead(s) to pace and/or sense the left atrium, a right ventricle lead to pace and/or sense the right ventricle, and a left ventricle lead fed through the coronary sinus to a position to pace and/or sense the left ventricle. Pulmonary artery lead(s) is (are) capable of being used to transvascularly stimulate target parasympathetic nerves anatomically located proximate to the left and right pulmonary artery at a strength sufficient to elicit depolarization of adjacent nerves, and is (are) also capable of being used to deliver left and right atrial pacing pulses, for example. Such atrial pacing can be provided in some CRT applications.

According to various embodiments, the device is designed to sense a refractory period, and to deliver the neural stimulation from an electrode or electrodes within the pulmonary artery during the refractory period to avoid unintentionally capturing cardiac tissue and inducing an arrhythmia such as atrial fibrillation. The myelinated vagal nerve fibers of a parasympathetic nervous system is much lower than that of myocardial tissue. Thus, when stimulating these myelinated vagal nerve fibers, parasympathetic stimulation can be applied in the absence of myocardial stimulation.

Various lead embodiments implement a number of designs, including an expandable stent-like electrode with a mesh surface dimensioned to abut a wall of a predetermined blood vessel, a coiled electrode(s), a fixed screw-type electrode(s), and the like. Various embodiments place the electrode(s) inside the blood vessel, into the wall of the blood vessel, or a combination of at least one electrode inside the blood vessel and at least one electrode into the wall of the blood vessel. The neural stimulation electrode(s) can be integrated into the same lead used for CRT or in another lead in addition to CRT lead(s).

Increased sympathetic nervous system activity following ischemia often results in increased exposure of the myocardium to epinephrine and norepinephrine. These catecholamines activate intracellular pathways within the myocytes, which lead to myocardial death and fibrosis. Stimulation of the parasympathetic nerves inhibits this effect. According to various embodiments, the present subject matter selectively activates the vagal cardiac nerves in addition to CRT in heart failure patients to protect the myocardium from further remodeling and arrhythmogenesis.

Figure 10:
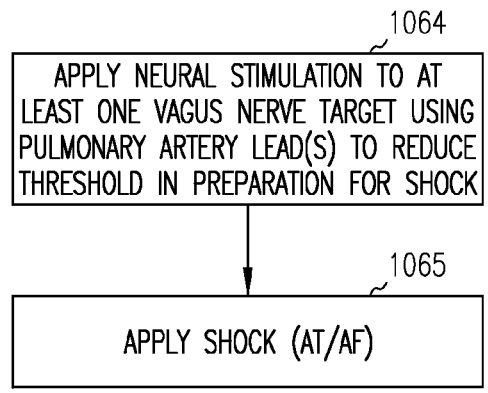
FIG. 10 illustrates an embodiment of a method to reduce a defibrillation threshold using neural stimulation of a vagus nerve target from a pulmonary artery lead.

FIG. 10 illustrates an embodiment of a method to reduce a defibrillation threshold using neural stimulation of a vagus nerve target from a pulmonary artery lead. Such a method can significantly reduce the pain associated with applying electrical shocks. At 1064, neural stimulation is applied to at least one vagus nerve target using pulmonary artery lead(s) to reduce threshold in preparation for an electrical shock, such as a defibrillation shock. At 1065, the electrical shock therapy is applied.

Figure 11:
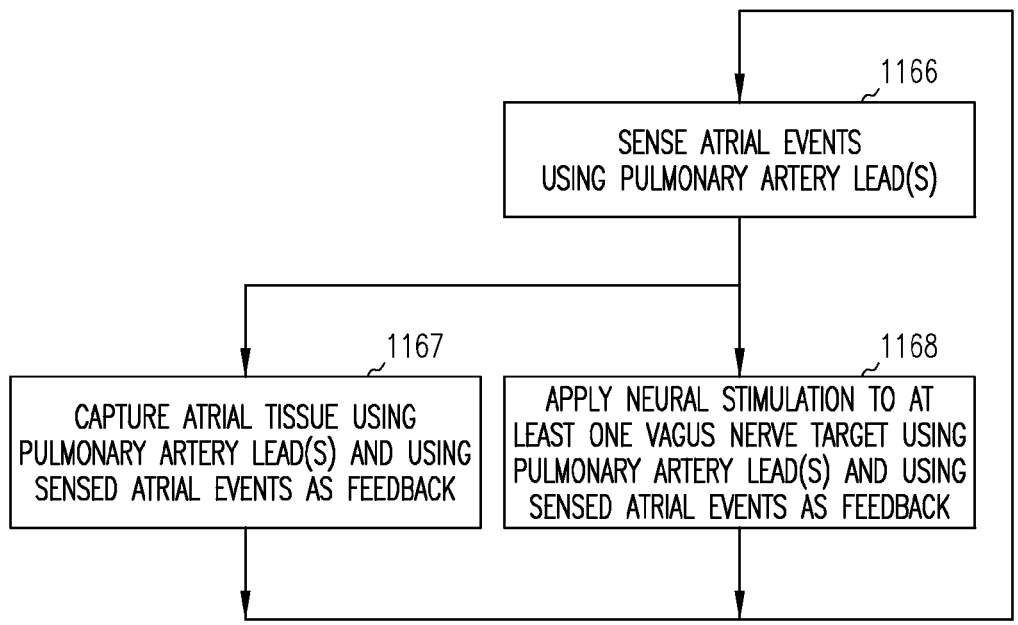
FIG. 11 illustrates an embodiment of a method to pace atrial tissue using pulmonary artery lead(s).

FIG. 11 illustrates an embodiment of a method to pace atrial tissue using pulmonary artery lead(s). At 1166, pulmonary artery lead(s) are used to sense atrial event(s). In some embodiments as illustrated in 1167, atrial tissue is captured using pulmonary artery lead(s), and using the sensed atrial events as feedback for controlling the capture of atrial tissue. The atrial sensing and atrial stimulation can be provided using the same electrode locations or different electrode locations such as in the right and left pulmonary arteries. In some embodiments as illustrated at 1168, neural stimulation is applied to at least one vagus nerve target using the pulmonary artery lead(s) and using the sensed atrial events as feedback for the applied neural stimulation. The atrial sensing and neural stimulation can be provided using the same electrode locations or different electrode locations such as in the right and left pulmonary arteries. Some embodiments use sensed atrial events as feedback for both neural stimulation and atrial pacing.

Illustrated Pre-Formed Lead Embodiments

The pulmonary artery lead includes one or more conductors, such as coiled conductors or other conductors, to conduct electrical energy from the pulse generator, and in some embodiments to receive intrinsic signals. The lead further includes outer insulation to insulate the conductor. The conductor(s) are connected to electrode(s). Lead terminal pins are attached to pulse generator. The system can include unipolar configurations with the case of the pulse generator acting as an electrode or a bipolar system with a pulse between or among two or more electrodes, located on the same or on different leads. Electrodes can include pacing/sensing electrodes, such as ring and/or tip electrodes, and can further include a shocking electrode, such as a coil electrode, capable of defibrillation.

The pulmonary artery lead can be configured to allow a stylet, guidewire, and/or catheter delivery. For example, an opening can be left through the middle of the lead to allow a stylet to be used. In an embodiment of a bifurcated lead, the lead body includes a first lumen through an entire length of the first portion and the first branch of the lead body, and a second lumen through an entire length of the first portion and the second branch of the lead body to allow the lead to be implanted over a guide wire. An anti-thrombosis coating can be placed on at least a portion of a lead. Various embodiments of the lead have at least a portion covered with an anti-thrombosis covering, such as a Hypren or polyethyleneglycol anti-thrombosis coating. The anti-thrombosis covering can be placed on the coil electrode or on other segments of the lead.

The distal end of the pulmonary artery lead, or branches of the pulmonary artery lead, is securely positioned to securely position the electrode(s) within the pulmonary artery. According to various embodiments, the distal end of lead includes a pre-formed, biased shape adapted to passively fixate distal end of the lead within the pulmonary artery or a branch thereof. In some embodiments, the pre-formed biased shape includes an S-shaped configuration. Some lead embodiments use a pre-formed biased shape with a curved shape such as an S-shape, a C-shape, a J-shape, an O-shape, and other non-linear shapes adapted for contacting one or more sides of the pulmonary artery to provide sufficient fixation of the lead. The passive fixation due to the shape of the distal portion of the lead is relatively easy to implant and explant. Passive fixation allows for easier adjustment of electrode placement. To form the pre-formed biased shape, the lead body can be manufactured in the pre-biased shape or the conductor coil can be formed in the pre-biased shape to thus bias the lead body. Some embodiments use an active fixation technique, and some embodiments use neither passive nor active fixation, relying on the shape and gravity to hold the electrode(s) in place within the pulmonary artery.

Figure 12:
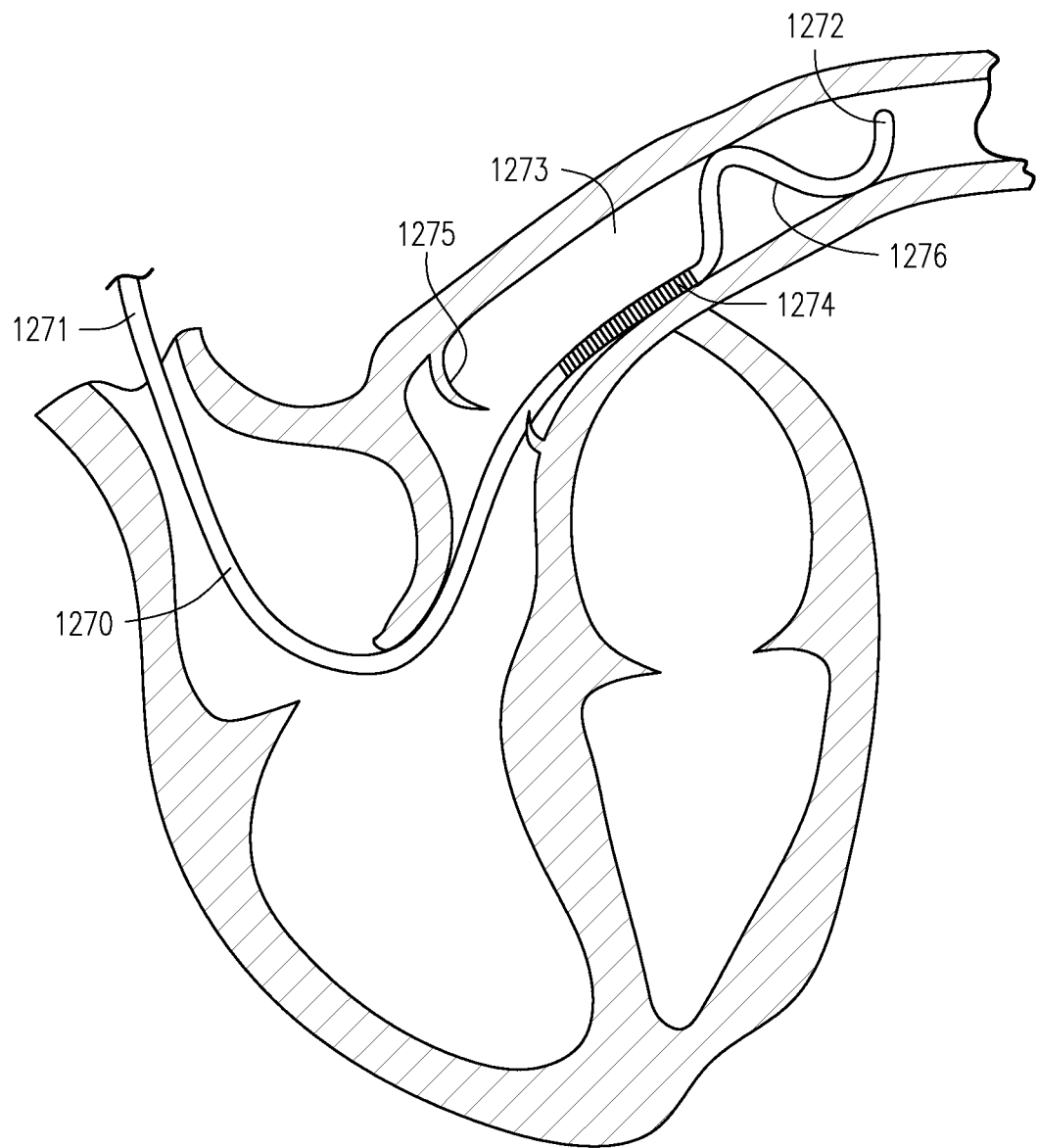
FIG. 12 shows a view of a lead, according to various embodiments, implanted within a heart.

FIG. 12 shows a view of a lead, according to various embodiments, implanted within a heart. Lead 1270 extends from a proximal end 1271 to a distal end 1272. Lead 1270 can be implanted in heart with distal end 1272 located within the pulmonary artery 1273 and electrode 1274 positioned within the pulmonary artery 1273 past the pulmonary artery valve 1275. Some embodiments utilize a branch of the pulmonary artery for fixation of distal end. The lead 1270 includes a pre-formed, biased shape 1276 on distal end 1272 of lead. Pre-formed biased shape 1276 can include a curved shape such as an S-shape, a C-shape, a J-shape, an O-shape, and other non-linear shapes adapted for contacting one or sides of the pulmonary artery (or a branch of the pulmonary artery) to provide sufficient fixation of the lead. The lead is easier to implant and explant because of the passive fixation which is allowed by shape of distal portion of lead. For example, passive fixation allows for easier adjustment of electrode placement, and is easier to explant. Moreover, there is less trauma or perforation to endocardium tissue than with active fixation leads, which can yield lower pacing thresholds.

Figure 13:
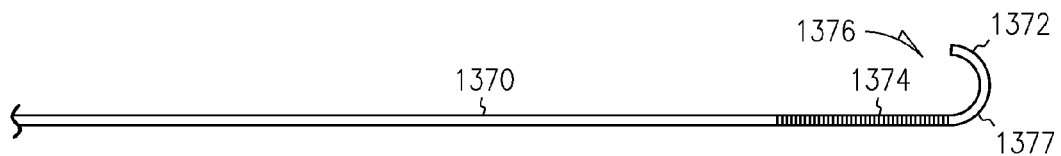
FIG. 13 shows a distal portion of a lead according to one embodiment.

FIG. 13 shows a distal portion of a lead 1370 according to one embodiment. In this example, pre-formed, biased shape 1376 includes a J-shaped curve 1377 at a distal tip 1372 of the lead body. J-shaped curve can be positioned within pulmonary artery or in one of the branch arteries off of the pulmonary artery to fixate the distal end of the lead within the pulmonary artery. The electrode 1374 is positioned along the lead a distance from the pre-formed, biased shape 1376 such that, when the lead is positioned and secured within the pulmonary artery, the electrode is capable of being positioned to stimulate a vagal nerve target, capture atrial tissue, sense atrial events, or combinations thereof. More than one electrode can be used.

Figure 14:
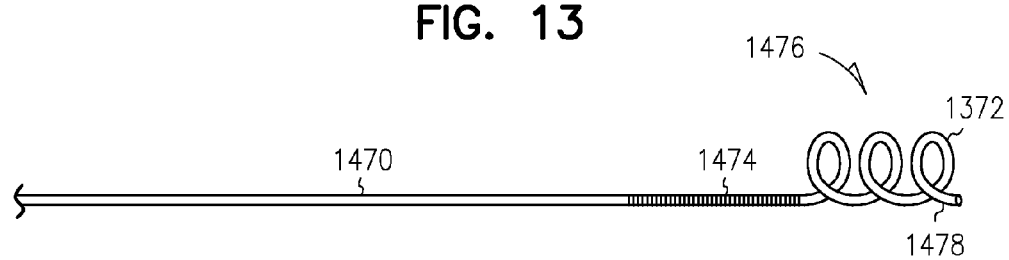
FIG. 14 shows a distal portion of a lead according to one embodiment.

FIG. 14 shows a distal portion of a lead 1470 according to one embodiment. In this example, pre-formed, biased shape 1476 includes a spiral configuration 1478 at or near the distal portion 1372. The pre-formed, biased shape generally can include at least two lead surfaces which are dimensioned and positionable such that the surfaces contact opposing walls of the pulmonary artery. The electrode 1474 is positioned along the lead a distance from the pre-formed, biased shape 1476 such that, when the lead is positioned and secured within the pulmonary artery, the electrode is capable of being positioned to stimulate a vagal nerve target, capture atrial tissue, sense atrial events, or combinations thereof. More than one electrode can be used.

Figure 15:
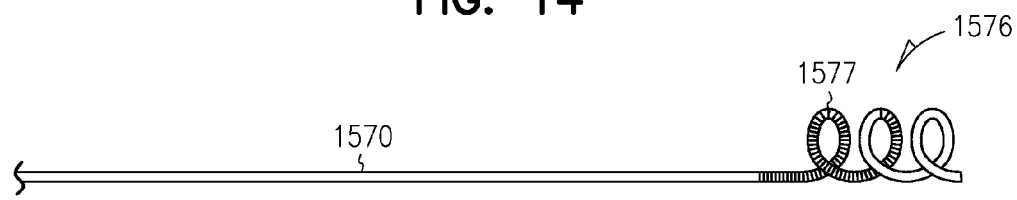
FIG. 15 shows lead having a spiral configuration which partially includes a coil electrode formed into a coil shape and at least partially defining the spiral configuration.
Figure 16:
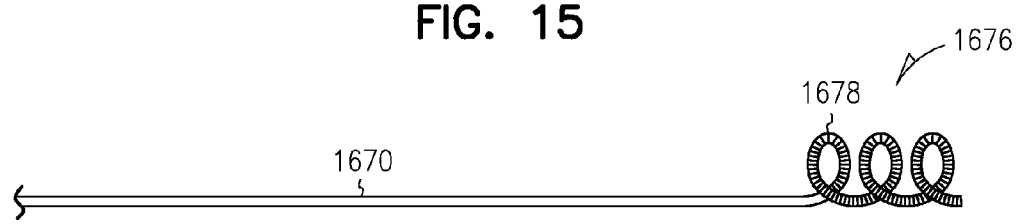
FIG. 16 shows lead having a spiral configuration and a coil electrode covers the distal end of the lead.

The pre-formed biased shapes discussed above and below can also be formed at least partly by the coil electrode itself. For example, FIG. 15 shows lead 1570 having a spiral configuration 1576 which partially includes a coil electrode 1577 formed into a coil shape and at least partially defining the spiral configuration. FIG. 16 shows lead 1670 having a spiral configuration 1676 and a coil electrode 1678 covers the distal end of the lead. In these examples of FIGS. 15 and 16, the coil electrodes can be pre-formed in the spiral shape to bias the distal end of the lead into the spiral configuration.

Figure 17:
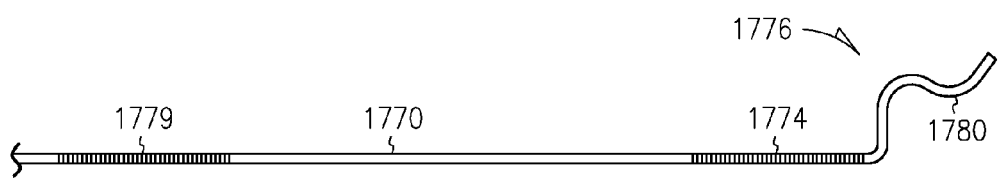
FIG. 17 shows a view of a lead, according to one embodiment.

FIG. 17 shows a view of a lead, according to one embodiment. Lead 1770 includes a second electrode 1779, such as the illustrated coil electrode or another electrode such as a ring electrode, in addition to a first electrode 1774. In this example, pre-formed, biased shape 1776 includes a modified S-shaped configuration 1780 to hold the lead within the pulmonary artery or a branch of the pulmonary artery. Multiple electrodes on the lead can be positioned within the pulmonary artery. Some electrode(s) can be positioned within the right atrium and/or right ventricle, and some electrode(s) can be positioned within the left and/or right pulmonary artery.

Figure 18:
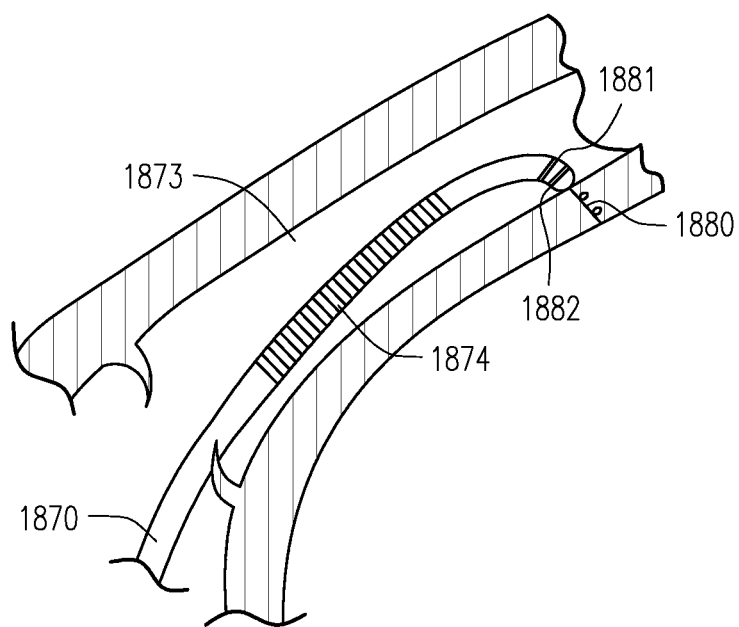
FIG. 18 shows a view of a lead, according to one embodiment, implanted within a heart.

FIG. 18 shows a view of a lead, according to one embodiment, implanted within a heart. Lead 1870 is adapted to be actively fixated within the pulmonary artery 1873 utilizing a helix 1880 or other fixation mechanism, for example. Lead includes electrode 1874 which is positionable to apply energy pulses to atrial tissue and/or vagal nerve targets. Some lead embodiment include radiopaque markers 1881 near the distal tip to help a physician guide the lead when viewed under fluoroscopy. One embodiment includes a drug elution member 1882, which can elute steroids, for example, to reduce inflammatory response of the tissue. In some embodiments, active fixation can be provided in addition to or in place of the passive fixation design discussed above.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined, and those of skill in the art, upon reading and comprehending this disclosure, would understand how to appropriately combine illustrated embodiments. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A system comprising an implantable medical device (IMD) and a lead configured to be connected to the IMD, the lead comprising:
   a lead body having an end adapted to connect to the IMD and a distal portion adapted to be securely positioned in a pulmonary artery;
   the lead body being adapted to be fed into the right atrium, through a tricuspid valve, into a right ventricle, and through a pulmonary valve; and
   the distal portion of the lead body being adapted to be secured within a pulmonary artery, the distal portion including at least one electrode adapted to be positioned within the pulmonary artery when the distal portion is secured within the pulmonary artery, wherein the IMD is adapted to use the at least one electrode to:
apply neural stimulation to a neural stimulation target when the distal portion is secured within the pulmonar artery; and
capture atrial tissue when the distal portion is secured within the pulmonary artery, or sense an intrinsic atrial electrical event when the distal portion is secured within the pulmonary artery, or both capture atrial tissue and sense an intrinsic atrial electrical event when the distal portion is secured within the pulmonary artery.

2. The system of claim 1, wherein the distal portion of the lead body includes a pre-formed, biased shape adapted to passively fixate the distal end of the lead body within the pulmonary artery.

3. The system of claim 2, wherein the pre-formed, biased shape includes an S-shaped configuration.

4. The system of claim 2, wherein the pre-formed, biased shape includes a C-shaped configuration.

5. The system of claim 2, wherein the pre-formed, biased shape includes a spiral configuration.

6. The system of claim 2, wherein the pre-formed, biased shape includes a J-shaped configuration.

7. The system of claim 2, wherein the pre-formed, biased shape includes at least one curve in the lead body dimensioned to provide at least two surfaces positioned to contact opposing walls of the pulmonary artery.

8. The system of claim 1, wherein the at least one electrode includes a defibrillation coil electrode.

9. The system of claim 1, wherein the at least one electrode includes a stent-like electrode adapted to expand into contact with a pulmonary artery wall, the expanded stent-like electrode being passively-fixed within the pulmonary artery.

10. The system of claim 1, wherein the at least one electrode includes a ring electrode or a tip electrode.

11. The system of claim 1, wherein the lead body includes a lumen through an entire length of the lead body to allow the lead to be implanted over a guide wire.

* * * * *